United States Patent
Heymans et al.

(10) Patent No.: US 6,531,476 B1
(45) Date of Patent: Mar. 11, 2003

(54) PIPERAZINE DERIVATIVES INHIBITING HUMAN IMMUNODEFICIENCY VIRUS REPLICATION

(75) Inventors: Francoise Heymans, Paris (FR); Nathalie Dereuddre-Bosquet, Paris (FR); Jean-Jacques Godfroid, Paris (FR); Aazdine Lamouri, Le Blanc Mesnil (FR); Pascal Clayette, Versailles (FR); Marc Martin, Flins (FR)

(73) Assignees: Universite Paris 7 - Denis Diderot, Paris (FR); Commissariat a l'Energie Atomique, Paris (FR)

( * ) Notice: Subject to any disclaimer, the term of this patent is extended or adjusted under 35 U.S.C. 154(b) by 0 days.

(21) Appl. No.: 09/720,921
(22) PCT Filed: Jul. 5, 1999
(86) PCT No.: PCT/FR99/01615
§ 371 (c)(1), (2), (4) Date: Mar. 20, 2001
(87) PCT Pub. No.: WO00/01677
PCT Pub. Date: Jan. 13, 2000

(30) Foreign Application Priority Data

Jul. 6, 1998 (FR) ............................................. 98/08600

(51) Int. Cl.[7] ..................... A61K 31/495; A61K 31/496; C07D 241/04; C07D 401/12; C07D 403/12
(52) U.S. Cl. ........................... 514/255.01; 514/253.01; 514/254.01; 544/365; 544/372; 544/387; 544/391
(58) Field of Search ................................ 544/391, 387, 544/365, 372; 514/255.01, 253.01, 254.01

(56) References Cited

U.S. PATENT DOCUMENTS

| | | | |
|---|---|---|---|
| 4,923,870 A | | 5/1990 | Braquet et al. |
| 4,927,825 A | * | 5/1990 | Pirotzky et al. ............ 514/255 |
| 5,019,576 A | | 5/1991 | Braquet et al. |

FOREIGN PATENT DOCUMENTS

| | | | |
|---|---|---|---|
| EP | 0 368 670 A | 5/1990 | |
| FR | 2 637 499 A | 4/1990 | |
| FR | 2 637 592 A | 4/1990 | |
| FR | 2 645 859 A | 10/1990 | |
| WO | WO 95 16688 A | 6/1995 | |

OTHER PUBLICATIONS

Tavet et al., "Design and modeling of new platelet–activating factor antagonists. 2. Synthesis and biological activity of 1,4–bis–(3',4',5'–trimethoxybenzoyl)–2–alkyl and 2–alkyloxymethylpiperazines." *J. Lipid Mediat. Cell Signal*, 1996, 15(2), pp. 145–159.

Batt et al., "New hypothesis on the conformation of the PAF–receptor from studies on the geometry of selected platelet–activating factor–antagonists." *J. Lipid Mediat.*, 1991, 4(3) pp. 343–346.

Binisty et al., "Structure–activity relationships in platelet activating factor. 9. From PAF–antagonism to PLA2 inhibition." *J. Lipid Mediat. Cell Signal*, 1996, 15(2) pp. 125–144.

François Heymans, George Dive, Aazdine Lamouri, Tounes Bellahsene, Estéra Touboul, Jack Huet, Fabrice Tavet, Catherine Redeuilh, Jean–Jacques Godfroid; *Design and modeling of a new platelet–activating factor antagonists. 3. Relative importance of hydrophobicity and electronic distribution in piperazinic series*; J. Lipid Mediators Cell Signalling; 1996; 161–173; 15(2), Coden: JLMSEO; ISSN: 0929–7855; XP002102680.

F. Heymans, A. Lamouri, J.–P. Batt; G. Dive; J.J. Godfroid; *Design and Modelling of new PAF Antagonists: 1,4–bis–(3', 4',5'–trimethoxybenzoyl)–2–substituted carbonyloxymethyl piperazines*; J. Lipid Mediators Cell Signalling; 1994; 153–154; 10(1–2); Coden: JLMSEO; ISSN: 0929–7855; XP002102681.

Aazdine Lamouri, Françoise Heymans, Fabrice Tavet, Georges Dive, Jean–Pierre Batt, Nicole Blavet, Pierre Braquet, and Jean–Jazues Godfroid; *Design and Modeling of New Platelet–Activating Factor Antagonists. 1. Syntehsis and Biological Activity of 1,4–Bis(3',4',5'–trimethoxybenzoyl)–2–[[(substituted carbonyl and carbamoyl) oxy]methyl] piperazines*; J. Med Chem; 1993;990–1000; 36(8); Coden: JMCMAR; ISSN: 0022–2623; XP002102682.

* cited by examiner

Primary Examiner—Emily Bernhardt
(74) Attorney, Agent, or Firm—Alston & Bird LLP

(57) ABSTRACT

The invention concerns the use of a piperazine derivative of formula (I)

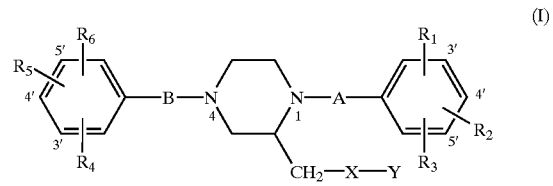

wherein: A and B=C=O, C=S or $CR_7R_8$ with $R_7$=H, methyl, cyano, cyanomethyl, $CO_2CH_3$ or (C=O)$CH_3$ and $R_8$=H or phenyl; $R_1$ to $R_6$=H, OH, or $C_1$-$C_5$ alkoxy; X represents: either C=O, O(C=O), O(C=S), O(SO$_2$), NH(C=O), NH(C=S), NH(SO$_2$), S(C=O) or S(C=S), then Y=NR$_9$R$_{10}$, CR$_9$R$_{10}$R$_{11}$ in which R$_9$, R$_{10}$ and R$_{11}$=H, $C_1$-$C_5$ alkyl, $C_2$-$C_5$ alkenyl, or $C_2$-$C_5$ alkynyl or Y=nitrogenous heterocycle comprising 5 to 10 atoms; or X represents O, S, O(C=O)O, NH(C=O)O, or S(C=O)O, then Y=CR$_9$R$_{10}$R$_{11}$ with R$_9$, R$_{10}$, R$_{11}$ as above; or one of its pharmaceutically acceptable salts for preparing a medicine inhibiting HIV. The invention is useful for treating HIV infection.

17 Claims, 2 Drawing Sheets

PIPERAZINE DERIVATIVES INHIBITING HUMAN IMMUNODEFICIENCY VIRUS REPLICATION

FIELD AND BACKGROUND OF THE INVENTION

The invention relates to piperazine derivatives for inhibiting the replication of Human Immunodeficiency Virus.

Besides inducing a breakdown of the immune defences, reflected in infected patients by the occurrence of serious opportunist infectious diseases, infection with Human Immunodeficiency Virus (HIV), the major cell targets of which are the CD4+ T lymphocytes and the cells of the macrophage line, is responsible for a chronic inflammatory syndrome, most particularly in the central nervous system, which is manifested by neurological complications which are grouped together under the name HIV encephalopathy or subacute encephalitis. "Platelet Activating Factor" (PAF), which has been identified as an early mediator of inflammation and allergy, appears to play an essential role in this inflammatory syndrome, not only on account of its role as an inflammation mediator, but also by means of its neurotoxicity.

The efficacy of a treatment in HIV infection is measured by the reduction of the viral load in the blood of the infected patients and by the restoration of the level of circulating CD4+ T lymphocytes. With respect to these criteria, two classes of anti-retroviral agents acting at two different steps in viral replication have been found to be effective to date and consequently form the basis of the current treatment of HIV infection. These are:

firstly, reverse transcriptase inhibitors which are directed toward inhibiting the activity of the viral enzyme which ensures the retrotranscription of the viral ribonucleic acid (RNA) into deoxyribonucleic acid (DNA), this being the form in which the virus passes into the nucleus of the infected cell and becomes incorporated into its cell genome. These reverse transcriptase inhibitors are represented by zidovudine (AZT), didanosine (ddI), zalcitabine (ddC), lamivudine (3TC), stavudine (d4T) and nevirapine; and secondly, protease inhibitors such as indinavir, ritonavir, saquinavir and nelfinavir, which act by inhibiting the activity of a viral enzyme involved in the process of maturation of the viral particles derived from the replication—that is to say in the installation of their various internal proteins and enzymes —, this maturation process preceding the release of these particles toward other cells to be infected.

These anti-retroviral agents are usually used in combination: thus, triple therapy, which consists in combining two reverse transcriptase inhibitors and a protease inhibitor, is nowadays prescribed as the first line treatment, and quadruple-therapy protocols are currently under clinical evaluation.

Despite their value, the anti-retroviral agents currently available do not really solve the problem of HIV infection.

Specifically, firstly, they induce viral mutations which are responsible for the appearance of resistance to the treatment and, in the long term, for a phenomenon of therapeutic evasion resulting in a resumption of the infection. Furthermore, since the resistances induced are usually crossed between the various anti-retroviral agents, especially between the protease inhibitors, the therapeutic substitutions are very limited.

Secondly, some of these anti-retroviral agents are of limited diffusion in tissues. In particular, they are incapable of crossing the blood-brain barrier and consequently of reaching the central nervous system, which however constitutes a preferred target of the viral infection.

These anti-retroviral agents moreover have numerous side effects (anemia, leukopenia, nausea, vomiting, diarrhea, myalgia, headaches, peripheral neuropathy, skin rashes, fever, pancreatitis, liver toxicity, etc.), these effects being all the more pronounced when they are used in combination. Besides the possibility of these side effects resulting in patient non-compliance due to the inconvenience they cause to the patients, they may in certain cases impose stoppage of the treatment on account of the seriousness of their nature.

Finally, these anti-retroviral agents have the drawback of having limited activity on the virus itself and of being incapable of protecting or reestablishing the immune system of the infected patients.

The problem consequently arises, of providing compounds which, while being active on HIV and consequently suitable for effectively treating an infection with this virus, have broad diffusion in tissues and are especially capable of reaching the central nervous system, do not induce resistance and have no crossed resistance with the anti-retroviral agents currently used, make it possible not only to eliminate the virus but also to protect or even restore the immune system, and also have satisfactory tolerance which is compatible with optimal patient compliance.

1,4,-Bis(3',4',5'-trimethoxybenzoyl)-2-(N,N-methoxycarbonyl)-piperazine were disclosed in French patent application No. 89 13258 as anti-ischemic and anti-inflammatory agents.

Moreover, it was shown, in French patent applications No. 89 13259 and No. 90 04798 and in European patent application No. 0 368 670, that trisubstituted piperazine derivatives are capable of inhibiting in vitro the effects of PAF on blood platelet aggregation and, in this respect, can be used in the treatment of pathologies in which this mediator appears to be involved, and especially in the treatment of inflammatory syndromes and allergic syndromes (acute inflammations, gastrointestinal ulcerations, asthma, cardiac anaphylaxis, etc.).

The advantage of piperazine derivatives of this type as PAF antagonists was subsequently confirmed by the studies by Lamouri et al. (*J. Med. Chem.*, 1993, 36, 8, 990–1000) and Heymans et al. (*J. Lipid Mediators Cell Signalling*, 1994, 10, 153–154; *J. Lipid Mediators Cell Signalling*, 1996, 15, 161–173) which were directed toward specifying the influence of the chemical structure of these compounds on their biological activity.

Now, continuing their studies on piperazine derivatives, the Inventors have discovered that, surprisingly, in addition to having anti-PAF activity, some of these derivatives are capable of very efficiently inhibiting HIV replication, and are thus suitable as a therapy of choice in the treatment of HIV infection since they make it possible not only to block the multiplication of this virus within the body and its ultimate elimination, but also to restore the immune functions by virtue of their inhibitory activity toward PAF.

SUMMARY OF THE INVENTION

One subject of the present invention is thus the use of a piperazine derivative corresponding to the general formula (I):

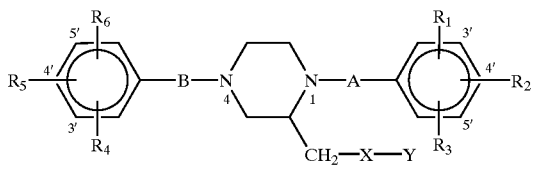

(I)

in which:

A and B represent, independently of each other, a C=O, C=S or $CR_7R_8$ group in which $R_7$ represents a hydrogen atom or a group chosen from methyl, cyano, cyanomethyl, $CO_2CH_3$ and $(C=O)CH_3$ groups, while $R_8$ represents a hydrogen atom or a phenyl group;

$R_1$, $R_2$, $R_3$, $R_4$, $R_5$ and $R_6$ represent, independently of each other, a hydrogen atom, a hydroxyl group or a linear or branched $C_1$–$C_5$ alkoxy group;

X represents:

either a group chosen from C=O, O(C=O), O(C=S), $O(SO_2)$, NH(C=O), NH(C=S), $NH(SO_2)$, S(C=O) and S(C=S) groups, in which case Y represents either a group $NR_9R_{10}$ or $CR_9R_{10}R_{11}$ in which $R_9$, $R_{10}$ and $R_{11}$ represent, independently of each other, a hydrogen atom, a linear or branched $C_1$ to $C_5$ alkyl, $C_2$ to $C_5$ alkenyl or $C_2$ to $C_5$ alkynyl group, or a nitrogen heterocycle comprising from 5 to 10 atoms and optionally one or more heteroatoms chosen from nitrogen, oxygen and sulfur;

or an oxygen or sulfur atom or a group chosen from O(C=O)O, NH(C=O)O and S(C=O)O groups, in which case Y represents a group $CR_9R_{10}R_{11}$ in which $R_9$, $R_{10}$ and $R_{11}$ have the same meaning as above;

or one of the pharmaceutically acceptable salts thereof, for the preparation of a medicinal product for inhibiting the replication of human immunodeficiency virus (HIV).

In the text hereinabove and hereinbelow:

the expression "linear or branched $C_1$ to $C_5$ alkyl group" denotes any hydrocarbon-based group containing not more than 5 carbon atoms, such as a methyl, ethyl, propyl, isopropyl, butyl, isobutyl, tert-butyl or pentyl group;

the expression "linear or branched $C_2$ to $C_5$ alkenyl group" denotes any hydrocarbon-based group containing from 2 to 5 carbon atoms and one or more carbon-carbon double bonds, such as a vinyl, allyl, butenyl, butadienyl or pentenyl group;

the expression "linear or branched $C_2$ to $C_5$ alkynyl group" denotes any hydrocarbon-based group comprising from 2 to 5 carbon atoms and one or more carbon-carbon triple bonds, such as an ethynyl, propynyl, butynyl or pentynyl group;

the expression "linear or branched $C_1$ to $C_5$ alkoxy group" denotes any group of formula OR in which R represents a saturated or unsaturated hydrocarbon-based chain containing not more than 5 carbon atoms, such a methoxy, ethoxy, propoxy, isopropoxy, butoxy, tert-butoxy, pentoxy, allyloxy, butenyloxy, methylpropenyloxy, pentenyloxy, methylbutenyloxy or pentadienyloxy group, and the expression "nitrogen heterocycle containing from 5 to 10 atoms and optionally one or more other heteroatoms chosen from nitrogen, oxygen and sulfur" denotes any saturated or unsaturated ring containing from 5 to 10 atoms, at least one of which is a nitrogen atom, and optionally containing one or more other atoms chosen from nitrogen, oxygen and sulfur, such as pyrrolyl, imidazolyl, pyrazolyl, triazolyl, tetrazolyl, pyrrolidinyl, pyrazolidinyl, imidazolidinyl, piperidyl or indolyl group.

In accordance with the invention, $R_1$, $R_2$ and $R_3$ are preferably borne by the carbon atoms in positions 3',4' and 5' of the phenyl nucleus linked to the group A, while $R_4$, $R_5$ and $R_6$ are preferably borne by the carbon atoms in positions 3',4' and 5' of the phenyl nucleus linked to the group B.

According to a first preferred embodiment of the invention, the piperazine derivative corresponds to the specific formula (I-a):

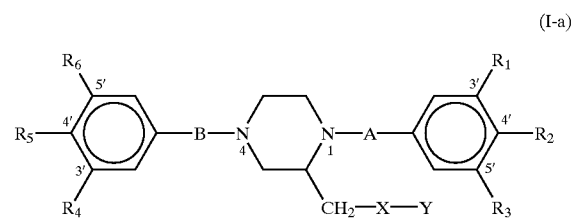

(I-a)

in which A and B represent, independently of each other, a C=O or C=S group, while $R_1$, $R_2$, $R_3$, $R_4$, $R_5$, $R_6$, X and Y have the same meaning as in the general formula (I) defined above.

Advantageously, in the specific formula (I-a), $R_1$, $R_2$, $R_4$ and $R_5$ represent a methoxy group, $R_3$ and $R_6$ both represent a hydrogen atom or a methoxy group, X represents:

either an O(C=O) or NH(C=O) group, in which case Y represents a group $NR_9R_{10}$ or $CR_9R_{10}R_{11}$ in which $R_9$, $R_{10}$ and $R_{11}$ have the same meaning as in the general formula (I) above, or alternatively a nitrogen heterocycle containing from 5 to 10 atoms and optionally one or more other heteroatoms chosen from nitrogen, oxygen and sulfur;

or an NH(C=O)O group, in which case Y represents a group $CR_9R_{10}R_{11}$ in which $R_9$, $R_{10}$ and $R_{11}$ have the same meaning as in the general formula (I) above.

The piperazine derivative corresponding to the specific formula (1-a) is preferably chosen from 1,4-bis(3',4',5'-trimethoxybenzoyl)-2-(N,N-diethylaminocarbonyloxymethyl)piperazine, 1,4-bis(3',4',5'-trimethoxybenzoyl)-2-(N,N-dipropylaminocarbonyloxymethyl)piperazine, 1,4-bis(3',4',5'-trimethoxybenzoyl)-2-(1'-piperidinocarbonyloxymethyl)piperazine, 1,4-bis(3',4',5'-trimethoxybenzoyl)-2-(1'-pyrrolidinocarbonyloxymethyl)piperazine, 1,4-bis(3',4'-dimethoxybenzoyl)-2-(N,N-diethylaminocarbonyloxymethyl)piperazine, 1,4-bis(3',4',5'-trimethoxybenzoyl)-2-(isopropyloxycarbonylaminomethyl)piperazine, 1,4-bis(3',4',5'-trimethoxybenzoyl)-2-(tert-butylcarbonylaminomethyl)piperazine, 1-(3',4',5'-trimethoxybenzoyl)-4-(3',4',5'-trimethoxythiobenzoyl)-2-(N,N-diethylaminocarbonyloxymethyl)piperazine, 1,4-bis(3',4',5'-trimethoxythiobenzoyl)-2-(N,N-diethylaminocarbonyloxymethyl)piperazine and 1-(3',4',5'-trimethoxythiobenzoyl)-4-(3',4',5'-trimethoxybenzoyl)-2-(N,N-diethylaminocarbonyloxymethyl)piperazine.

In a particularly preferred manner, the piperazine derivative corresponding to the specific formula (I-a) is 1,4-bis(3',4',5'-trimethoxybenzoyl)-2-(N,N-diethylaminocarbonyloxymethyl)piperazine.

According to another preferred embodiment of the invention, the piperazine derivative corresponds to the specific formula (I-b):

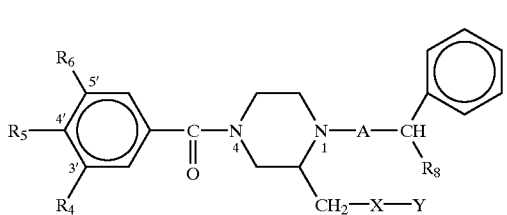

in which $R_8$ represents a hydrogen atom or a phenyl group, while $R_4$, $R_5$, $R_6$, X and Y have the same meaning as in the general formula (I) defined above.

Advantageously, in the specific formula (I-b), $R_4$, $R_5$ and $R_6$ represent a methoxy group, X represents an O(C=O) group, while Y represents a group $NR_9R_{10}$ in which $R_9$ and $R_{10}$ both represent a linear or branched $C_1$ to $C_5$ alkyl, $C_2$ to $C_5$ alkenyl or $C_2$ to $C_5$ alkynyl group, or alternatively a nitrogen heterocycle containing from 5 to 10 atoms and optionally one or more other heteroatoms chosen from nitrogen, oxygen and sulfur.

The piperazine derivative corresponding to the specific formula (I-b) is preferably chosen from 1-benzyl-4-(3',4',5'-trimethoxybenzoyl)-2-(N,N-diethylaminocarbonyloxymethyl)piperazine and 1-diphenylmethyl-4-(3',4',5'-trimethoxybenzoyl)-2-(N,N-diethylaminocarbonyloxymethyl)piperazine.

According to yet another preferred embodiment of the invention, the piperazine derivative corresponds to the specific formula (I-c):

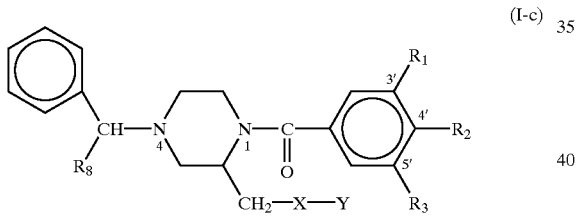

in which $R_8$ represents a hydrogen atom or a phenyl group, while $R_1$, $R_2$, $R_3$, X and Y have the same meaning as in the general formula (I) defined above.

Advantageously, in the specific formula (I-c), $R_1$, $R_2$ and $R_3$ represent a methoxy group, X represents an O(C=O) group, while Y represents a group $NR_9R_{10}$ in which $R_9$ and $R_{10}$ both represent a linear or branched $C_1$ to $C_5$ alkyl, $C_2$ to $C_5$ alkenyl or $C_2$ to $C_5$ alkynyl group, or a nitrogen heterocycle containing from 5 to 10 atoms and optionally one or more other heteroatoms chosen from nitrogen, oxygen and sulfur.

The piperazine derivative corresponding to the specific formula (I-c) is preferably 1-(3',4',5'-trimethoxybenzoyl)-4-benzyl-2-(N,N-diethylamino-carbonyloxymethyl)piperazine.

There are many advantages in using the piperazine derivatives of general formula (I) and the pharmaceutically acceptable salts thereof to prepare a medicinal product for inhibiting HIV replication. Specifically, besides being able to control the spread of the virus in infected patients and its ultimate elimination by virtue of their antiviral action, they are capable of inducing a reconstruction of the immune system of these patients by means of their inhibitory action on PAF activity. Moreover, although their mechanism of action on HIV replication has not yet been fully elucidated, these piperazine derivatives do not appear to act either on reverse transcriptase or on viral protease, and as such their use makes it possible to overcome problems of crossed resistance currently encountered by clinicians in the treatment of HIV infection. In addition, the piperazine derivatives that are useful in accordance with the invention show an absence of cytotoxicity, which argues in favor of a very satisfactory tolerance.

The piperazine derivatives of general formula (I) and the pharmaceutically acceptable salts thereof can be obtained by a process which comprises:

when the derivative which it is desired to prepare corresponds to the general formula (I) in which A and B are both a C=O group and when the phenyl nuclei to which they are attached bear the same substituents:

a) the acylation of a compound corresponding to the general formula (II) below:

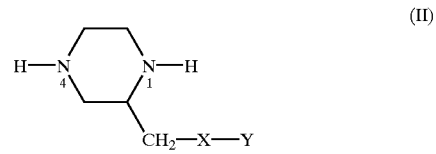

in which X and Y have the same meaning as in the general formula (I) defined above, with a reagent of general formula (III) below:

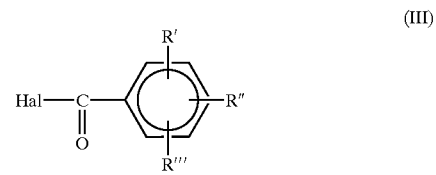

in which Hal represents a halogen atom and preferably a chlorine atom, while R', R" and R'" represent, independently of each other, a hydrogen atom, a hydroxyl group or a linear or branched $C_1$–$C_5$ alkoxy group, followed, if so desired, by b) the conversion of the compound obtained in step a) into a pharmaceutically acceptable salt thereof, when the derivative which it is desired to prepare corresponds to the general formula (I) in which A and B are both a C=O group and when the phenyl nuclei to which they are attached bear different substitutents:

a) the acylation of a compound corresponding to the general formula (II) as defined above, with a reagent of general formula (III-a) below, and then with a reagent of general formula (III-b) below:

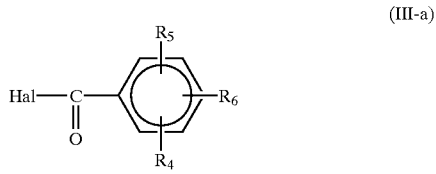

-continued

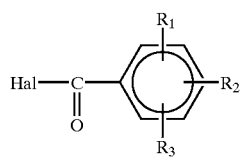
(III-b)

in which Hal represents a halogen atom and preferably a chlorine atom, while $R_1$, $R_2$, $R_3$, $R_4$, $R_5$ and $R_6$ have the same meaning as in the general formula (I) defined above, followed, if so desired, by
b) the conversion of the compound obtained in step a) into a pharmaceutically acceptable salt thereof;

when the derivative which it is desired to prepare corresponds to the general formula (I) in which A and B are both a C=S group and when the phenyl nuclei to which they are attached bear the same substitutents:
a) the acylation of a compound corresponding to the general formula (II) as defined above, with a reagent of general formula (III) as defined above,
b) the reaction of the compound obtained in step a) with a reagent capable of converting a carbonyl function into a thiocarbonyl function, such as, for example, Lawesson's reagent, followed, if so desired, by
c) the conversion of the compound obtained in step b) into a pharmaceutically acceptable salt thereof;

when the derivative which it is desired to prepare corresponds to the general formula (I) in which one of the two groups A and B is a C=O group, while the other is a C=S group, and when the phenyl nuclei to which they are attached bear the same substituents:
a) the acylation of a compound corresponding to the general formula (II) as defined above, with a reagent of general formula (III) as defined above, after having optionally protected (for example by tritylation) the nitrogen atom in position 4 of the piperazine ring of the compound,
b) the reaction of the compound obtained in step a) with a reagent capable of converting a carbonyl function into a thiocarbonyl function,
c) the acylation of the compound obtained in step b) with a reagent of general formula (III) as defined above, after deprotection (for example by detritylation) of the nitrogen atom in position 4 of the piperazine ring, if this atom was protected, followed, if so desired, by
d) the conversion of the compound obtained in step c) into a pharmaceutically acceptable salt thereof;

when the derivative which it is desired to prepare corresponds to the general formula (I) in which A is a C=O group, while B is a C=S group, and when the phenyl nuclei to which they are attached bear different substituents:
a) the acylation of a compound corresponding to the general formula (II) as defined above, with a reagent of general formula (III-a) as defined above,
b) the reaction of the compound obtained in step a) with a reagent capable of converting a carbonyl function into a thiocarbonyl function,
c) the acylation of the compound obtained in step b) with a reagent of general formula (III-b) as defined above, followed, if so desired, by
d) the conversion of the compound obtained in step c) into a pharmaceutically acceptable salt thereof;

when the derivative which it is desired to prepare corresponds to the general formula (I) in which A is a C=S group, while B is a C=O group, and when the phenyl nuclei to which they are attached bear different substituents:
a) the acylation of a compound corresponding to the general formula (II) as defined above, with a reagent of general formula (III-b) as defined above, after having protected the nitrogen atom in position 4 of the piperazine ring of this compound,
b) the reaction of the compound obtained in step a) with a reagent capable of converting a carbonyl function into a thiocarbonyl function,
c) the acylation of the compound obtained in step b) with a reagent of general formula (III-b) as defined above, after deprotection of the nitrogen atom in position 4 of the piperazine ring, followed, if so desired, by
d) the conversion of the compound obtained in step c) into a pharmaceutically acceptable salt thereof;

when the derivative which it is desired to prepare corresponds to the general formula (I) in which A and B are both a group $CR_7R_8$ and when the phenyl nuclei to which they are attached bear the same substituents:
a) the acylation of a compound corresponding to the general formula (II) as defined above, with a reagent of general formula (IV) below:

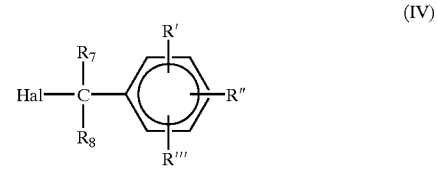
(IV)

in which Hal represents a halogen atom and, preferably a chlorine atom, $R_7$ and $R_8$ have the same meaning as in the general formula (I) defined above, while R', R" and R'" represent, independently of each other, a hydrogen atom, a hydroxyl group or a linear or branched $C_1$ to $C_5$ alkoxy group followed, if so desired, by
b) the conversion of the compound obtained in step a) into a pharmaceutically acceptable salt thereof;

when the derivative which it is desired to prepare corresponds to the general formula (I) in which A and B are both a group $CR_7R_8$ and when the phenyl nuclei to which they are attached bear different substituents:
a) the acylation of a compound corresponding to the general formula (II) as defined above with a reagent of general formula (IV-a) below, and then with a reagent of general formula (IV-b) below:

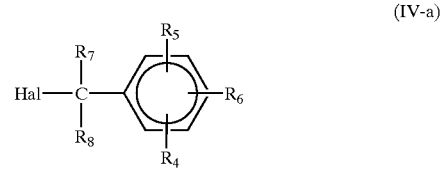
(IV-a)

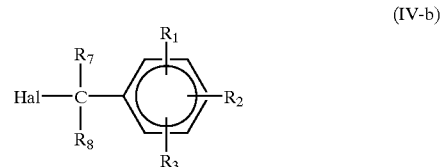
(IV-b)

in which Hal represents a halogen atom and preferably a chlorine atom, while $R_1$, $R_2$, $R_3$, $R_4$, $R_5$, $R_6$, $R_7$ and $R_8$ have the same meaning as in the general formula (I) defined above;

b) the conversion of the compound obtained in step a) into a pharmaceutically acceptable salt thereof;

when the derivative which it is desired to prepare corresponds to the general formula (I) in which one of the two groups A and B is a C=O group, while the other is a group $CR_7R_8$:

a) the acylation of a compound corresponding to the general formula (II) as defined above, with a reagent of general formula (III) as defined above, after having optionally protected the nitrogen atom in position 4 of the piperazine ring of this compound, b) the acylation of the compound obtained in step a) with a reagent of general formula (IV) as defined above, after deprotection of the nitrogen atom in position 4 of the piperazine ring when this atom has been protected, followed, if so desired, by c) the conversion of the compound obtained in step b) into a pharmaceutically acceptable salt thereof.

The compounds of general formula (II) in which X represents a O(C=O) group may be prepared from 1,4-dibenzyl-2-hydroxymethylpiperazine (which may be obtained by the process disclosed by Jucker and Rissi in *Helv. Chem. Acta*, 1962, 45, 2383–2402) by acylating this compound with an aryl halocarbonate such as phenyl chlorocarbonate, followed by subjecting the resulting compound to a substitution reaction by the action of a reagent of formula H—Y in which Y has the same meaning as in the general formula (II), and, finally, by subjecting the compound thus obtained to a hydrogenolysis, for example by means of palladium on active charcoal.

The compounds of general formula (II) in which X represents a O(C=S) group may also be prepared from 1,4-dibenzyl-2-hydroxymethylpiperazine, but in this case said compound is subjected to an addition-elimination reaction, for example by the successive action of thiophosgene and of a reagent of formula H—Y in which Y has the same meaning as in the general formula (II), followed by subjecting the resulting compound to a debenzylation, for example using 2,2,2-trichloroethyl chloroformate, and in the presence of zinc and acetic acid.

The compounds of general formula (II) in which X represents an $O(SO_2)$ group may also be obtained from 1,4-dibenzyl-2-hydroxymethylpiperazine by subjecting said compound to an addition-elimination reaction, for example by the successive action of sulfuryl chloride and a reagent of formula H—Y in which Y has the same meaning as in the general formula (II), followed by subjecting the resulting compound to a debenzylation.

The compounds of general formula (II) in which X represents an NH(C=O), NH(C=S) or NH(C=O)O group may be prepared from 1,4-dibenzyl-2-aminomethylpiperazine by reacting said compound with a reagent chosen from the reagents of formulae Hal(C=O)Y, Hal(C=S)Y and Hal(C=O)O—Y in which Hal represents a halogen atom, and preferably a chlorine atom, while Y has the same meaning as in the general formula (II), followed by subjecting the resulting compound to a hydrogenolysis, when X represents an NH(C=O) or NH(C=O)O group, and to a debenzylation, when X represents an NH(C=S) group.

The compounds of general formula (II) in which X represents an $NH(SO_2)$ group may also be prepared from 1,4-dibenzyl-2-aminomethylpiperazine, but in this case said compound is subjected to an addition-elimination reaction, for example by the successive action of sulfuryl chloride and of a reagent of formula H—Y in which Y has the same meaning as in the general formula (II), followed by a debenzylation.

1,4-Dibenzyl-2-aminomethylpiperazine may itself be obtained by reacting 2,3-dibromopropionitrile with N,N'-dibenzylethylenediamine in the presence of triethylamine and benzene, so as to obtain 1,4-dibenzyl-2-cyanopiperazine, followed by subjecting this compound to a reduction reaction, for example by the action of lithium aluminum hydride.

The compounds of general formula (II) in which X represents an S(C=O) group may be prepared from 1,4-dibenzyl-2-thiomethylpiperazine by acylating this compound with an aryl halocarbonate such as phenyl chlorocarbonate, followed by subjecting the resulting compound to a substitution reaction by the action of a reagent of formula H—Y in which Y has the same meaning as in the general formula (II), and finally, by subjecting the compound thus obtained to a debenzylation.

Similarly, the compounds of general formula (II) in which X represents an S(C=S) group may be prepared from 1,4-dibenzyl-2-thio-methylpiperazine by subjecting this compound to an addition-elimination reaction, for example by the successive action of thiophosgene and of a reagent of formula H—Y in which Y has the same meaning as in the general formula (II), and by subjecting the compound thus obtained to a debenzylation 1,4-Dibenzyl-2-thiomethylpiperazine may itself be obtained from 1,4-dibenzyl-2-chloromethylpiperazine by subjecting this compound to a nucleophilic substitution reaction, for example by means of sodium or potassium thioacetate, followed by saponifying the resulting compound with a base such as sodium hydroxide.

The compounds of general formula (II) in which X represents an oxygen atom or a sulfur atom may themselves be prepared, respectively, from 1,4-dibenzyl-2-hydroxymethylpiperazine and 1,4-dibenzyl-2-thiomethylpiperazine, by subjecting these compounds to an etherification, for example by the action of a base, and then of a reagent of formula Hal-Y in which Hal represents a halogen atom and preferably a chlorine atom, while Y has the same meaning as in the general formula (II) followed by subjecting the compound thus obtained to a hydrogenolysis.

The compounds of general formula (II) in which X represent either an O(C=O)O group or an S(C=O)O group may be obtained from 1,4-dibenzyl-2-hydroxymethylpiperazine and 1,4-dibenzyl-2-thiomethylpiperazine, respectively, by subjecting them to an addition-elimination reaction, for example by the action of a reagent of formula Hal(C=O)O—Y in which Hal represents a halogen atom and preferably a chlorine atom, while Y has the same meaning as in the general formula (II), followed by subjecting the resulting compounds to a debenzylation.

The present invention encompasses, for use in preparing a medicinal product intended to inhibit HIV replication, both known piperazine derivatives and piperazine derivatives that are novel per se.

A subject of the present invention is thus also novel piperazine derivatives which correspond to the general formula (I) as defined above, with the condition, however, that, in this general formula (I):

when $R_1$, $R_2$ and $R_3$ are saturated, linear or branched $C_1$ to $C_4$ alkoxy groups, and are borne by the carbon atoms located in positions 3',4' and 5' of the phenyl nucleus linked to the group A, and when B is a C=O group, Y is other than:

a linear or branched $C_1$ to $C_4$ alkyl, $C_2$ to $C_4$ alkenyl or $C_2$ to $C_4$ alkynyl group, when X represents an oxygen or sulfur atom; and a linear or branched $C_1$ to $C_4$ alkyl, $C_2$ to $C_4$ alkenyl or $C_2$ to $C_4$ alkynyl group, or an amine which is unsubstituted or substituted with one or two linear or branched $C_1$ to $C_4$ alkyl, $C_2$ to $C_4$ alkenyl or $C_2$ to $C_4$ alkynyl groups, when X represents a C=O or O(C=O) group;

when $R_1$, $R_2$, $R_3$, $R_4$, $R_5$ and $R_6$ all represent a methoxy group and when $R_1$, $R_2$ and $R_3$ are borne by the carbon atoms located in positions 3',4' and 5' of the phenyl nucleus linked to the group A, while $R_4$, $R_5$ and $R_6$ are borne by the carbon atoms located in positions 3',4' and 5' of the phenyl nucleus linked to the group B, Y is other than:

a linear or branched $C_5$ or $C_6$ alkyl group, an amine substituted with a linear or branched $C_5$ alkyl group, or an amine substituted with two linear $C_5$ alkyl groups, when A and B both represent a C=O group and X represents an O(C=O) group; and a group $CH(CH_2CH_3)_2$, when A and B both represent a $CH_2$ group and X represents an O(C=O) group;

as well as the pharmaceutically acceptable salts thereof.

In accordance with the invention, in these novel piperazine derivatives, $R_1$, $R_2$ and $R_3$ are preferably borne by the carbon atoms located in positions 3',4' and 5' of the phenyl nucleus linked to the group A, while $R_4$, $R_5$ and $R_6$ are preferably borne by the carbon atoms located in positions 3',4' and 5' of the phenyl nucleus linked to the group B.

According to a first preferred embodiment of these novel piperazine derivatives, said derivatives correspond to the specific formula (I-a):

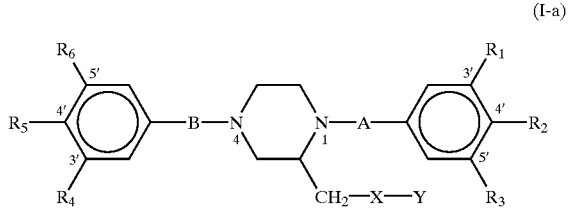

(I-a)

in which A and B represent, independently of each other, a C=O group or a C=S group, while $R_1$, $R_2$, $R_3$, $R_4$, $R_5$, $R_6$, X and Y have the same meaning as in the general formula (I) defined above, with the condition, however, that:

when $R_1$, $R_2$ and $R_3$ are saturated, linear or branched $C_1$ to $C_4$ alkoxy groups, and when B is a C=O group, Y is other than:

a linear or branched $C_1$ to $C_4$ alkyl, $C_2$ to $C_4$ alkenyl or $C_2$ to $C_4$ alkynyl group, when X represents an oxygen or sulfur atom; and a linear or branched $C_1$ to $C_4$ alkyl, $C_2$ to $C_4$ alkenyl or $C_2$ to $C_4$ alkynyl group, or an amine which is unsubstituted or substituted with one or two linear or branched $C_1$ to $C_4$ alkyl, $C_2$ to $C_4$ alkenyl or $C_2$ to $C_4$ alkynyl groups, when X represents a C=O or O(C=O) group;

when $R_1$, $R_2$, $R_3$, $R_4$, $R_5$ and $R_6$ all represent a methoxy group, Y is other than a linear or branched $C_5$ or $C_6$ alkyl group, an amine substituted with a linear or branched $C_5$ alkyl group, or an amine substituted with two linear $C_5$ alkyl groups, when X represents an O(C=O) group.

Among the novel piperazine derivatives of specific formula (I-a), the ones that are particularly preferred are those in which $R_1$, $R_2$, $R_4$ and $R_5$ represent a methoxy group, $R_3$ and $R_6$ both represent a hydrogen atom or a methoxy group, and X represents:

either an O(C=O) group, in which case Y represents a nitrogen heterocycle containing from 5 to 10 atoms and optionally one or more other heteroatoms chosen from nitrogen, oxygen and sulfur, or alternatively, when $R_3$ and $R_6$ represent a hydrogen atom, a group $NR_9R_{10}$ in which $R_9$ and $R_{10}$ both represent a linear or branched $C_1$ to $C_5$ alkyl, $C_2$ to $C_5$ alkenyl or $C_2$ to $C_5$ alkynyl group;

or an NH(C=O) group, in which case Y represents either a group $NR_9R_{10}$ or $CR_9R_{10}R_{11}$ in which $R_9$, $R_{10}$ and $R_{11}$ represent, independently of each other, a hydrogen atom or a linear or branched $C_1$ to $C_5$ alkyl, $C_2$ to $C_5$ alkenyl or $C_2$ to $C_5$ alkynyl group, or a nitrogen heterocycle containing from 5 to 10 atoms and optionally one or more other heteroatoms chosen from nitrogen, oxygen and sulfur;

or an NH(C=O)O group, in which case Y represents a group $CR_9R_{10}R_{11}$ in which $R_9$, $R_{10}$ and $R_{11}$ represent, independently of each other, a hydrogen atom or a linear or branched $C_1$ to $C_5$ alkyl, $C_2$ to $C_5$ alkenyl or $C_2$ to $C_5$ alkynyl group.

These novel piperazine derivatives of specific formula (I-a) are preferably 1,4-bis(3',4',5'-trimethoxybenzoyl)-2-(1'-piperidinocarbonyloxymethyl)piperazine, 1,4-bis(3',4',5'-trimethoxybenzoyl)-2-(1'-pyrrolidinocarbonyloxymethyl)piperazine, 1,4-bis(3',4'-dimethoxybenzoyl)-2-(N,N-diethylaminocarbonyloxymethyl)piperazine, 1,4-bis(3',4',5'-trimethoxybenzoyl)-2-(isopropyloxycarbonylaminomethyl)piperazine, 1,4-bis(3',4',5'-trimethoxybenzoyl)-2-(tert-butylcarbonylaminomethyl)piperazine, 1-(3',4',5'-trimethoxybenzoyl)-4-(3',4',5'-trimethoxythiobenzoyl)-2-(N,N-diethylaminocarbonyloxymethyl)piperazine and 1,4-bis(3',4',5'-trimethoxythiobenzoyl)-2-(N,N-diethylaminocarbonyloxymethyl)piperazine.

According to another preferred embodiment of these novel piperazine derivatives, said derivatives correspond to the specific formula (I-b):

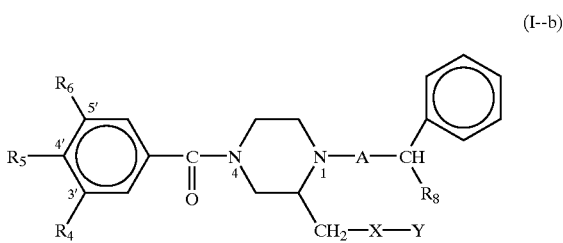

(I--b)

in which $R_8$ represents a hydrogen atom or a phenyl group, while $R_4$, $R_5$, $R_6$, X and Y have the same meaning as in the general formula (I) defined above.

Advantageously, in these novel piperazine derivatives of specific formula (I-b), $R_4$, $R_5$ and $R_6$ represent a methoxy group, X represents an O(C=O) group, while Y represents a group $NR_9R_{10}$ in which $R_9$ and $R_{10}$ both represent a linear or branched $C_1$ to $C_5$ alkyl, $C_2$ to $C_5$ alkenyl or $C_2$ to $C_5$ alkynyl group, or alternatively a nitrogen heterocycle containing from 5 to 10 atoms and optionally one or more other heteroatoms chosen from nitrogen, oxygen and sulfur.

The novel piperazine derivatives corresponding to the specific formula (I-b) are preferably 1-benzyl-4-(3',4',5'-trimethoxybenzoyl)-2-(N,N-diethylaminocarbonyloxymethyl)piperazine and 1-diphenylmethyl-4-(3',4',5'-trimethoxybenzoyl)-2-(N,N-diethylaminocarbonyloxymethyl)piperazine.

According to yet another preferred embodiment of said novel piperazine derivatives, these derivatives correspond to the specific formula (I-c);

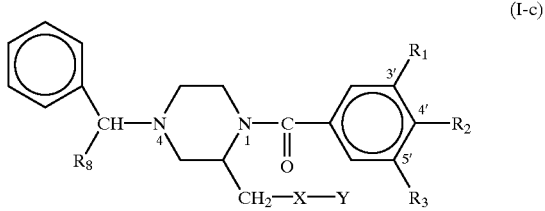

(I-c)

in which $R_8$ represents a hydrogen atom or a phenyl group, while $R_1$, $R_2$, $R_3$, X and Y have the same meaning as in the general formula (I) defined above.

Advantageously, in the novel piperazine derivatives of specific formula (I-c), $R_1$, $R_2$ and $R_3$ represent a methoxy group, X represents an O(C=O) group, while Y represents a group $NR_9R_{10}$ in which $R_9$ and $R_{10}$ both represent a linear or branched $C_1$ to $C_5$ alkyl, $C_2$ to $C_5$ alkenyl or $C_2$ to $C_5$ alkynyl group, or alternatively a nitrogen heterocycle containing from 5 to 10 atoms and optionally one or more other heteroatoms chosen from nitrogen, oxygen and sulfur.

Among these novel piperazine derivatives of specific formula (I-c), the one particularly preferred is 1-(3',4',5'-trimethoxybenzoyl)-4-benzyl-2-(N,N-diethylaminocarbonyloxymethyl)piperazine.

A subject of the present invention is also a novel piperazine derivative, which is 1-(3',4',5'-trimethoxythiobenzoyl)-4-(3',4',5'-trimethoxy-benzoyl)-2-(N,N-diethylaminocarbonyloxymethyl)piperazine, and the pharmaceutically acceptable salts thereof.

A subject of the present invention is also the novel piperazine derivatives as defined above, and the pharmaceutically acceptable salts thereof, for use as medicinal products.

A subject of the present invention is also pharmaceutical compositions, characterized in that they comprise as active principle at least one novel piperazine derivative as defined above, or a pharmaceutically acceptable salt thereof, and optionally excipients and additives taken from those conventionally used in pharmacy. Given the inhibitory properties shown by such a derivative, both on HIV replication and on the action of PAF, these pharmaceutical compositions especially find application in the prevention and/or treatment of HIV infection at all its stages: HIV-positive stage or Acquired Immunodeficiency Syndrome (AIDS) stage.

BRIEF DESCRIPTION OF THE DRAWINGS

Besides the preceding arrangements, the invention also comprises other arrangements which will emerge from the remainder of the description which follows, which relates to examples of the preparation of piperazine derivatives in accordance with the invention, and of demonstration of their inhibitory activity on HIV replication and of their absence of cytotoxicity, as well as to the attached drawings in which.

EXAMPLES

Figure 1:
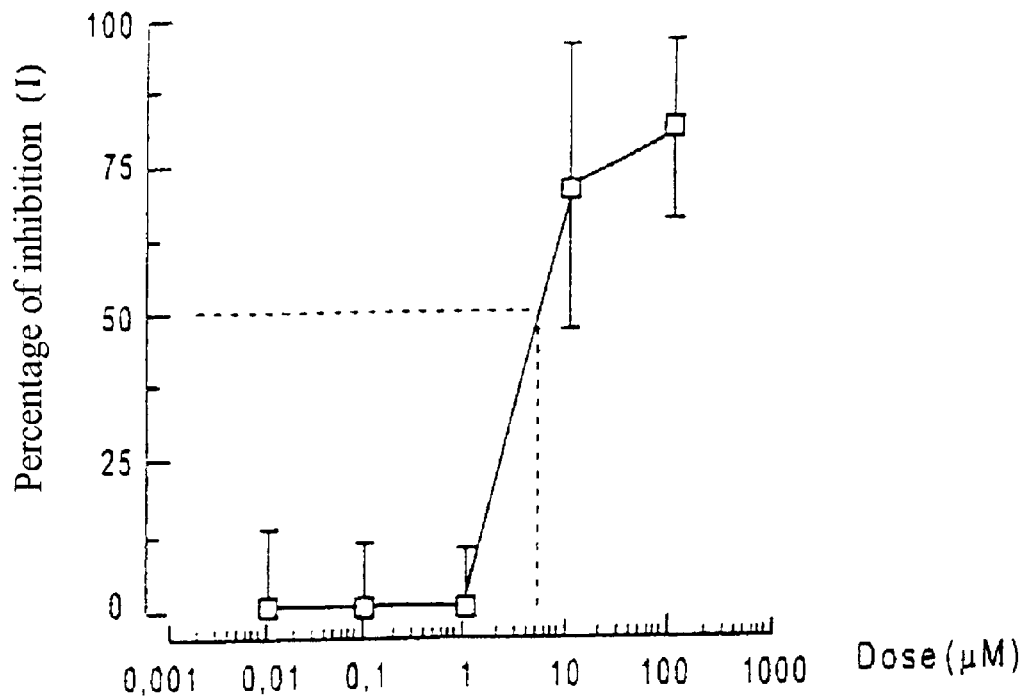
FIG. 1 illustrates, in the form of a curve, the dose-effect relationship of 1,4-bis(3',4',5'-trimethoxybenzoyl)-2-(N,N-diethylaminocarbonyloxymethyl)piperazine on HIV replication in monocyte-derived macrophages.

It should be clearly understood, however, that these examples are given purely for the purposes of illustrating the subject of the invention, and do not in any way constitute a limitation thereof.

I—Preparation of Piperazine Derivatives

Example 1

Preparation of 1,4-bis(3',4',5'-trimethoxybenzoyl)-2-(1'-pyrrolidinocarbonyloxymethyl)piperazine

[derivative of specific formula (I-a) in which A and B=C=O, $R_1$ to $R_6$=OCH$_3$, X=O(C=O) and Y=pyrrolidinyl]

1.1—Preparation of 1,4-dibenzyl-2-phenoxycarbonyloxymethylpiperazine

A solution comprising 10 g (33.7 mmol) of 1,4-dibenzyl-2-hydroxymethylpiperazine (prepared in accordance with the process described by Jucker and Rissi in *Helv. Chem. Acta*, 1962, 45, 2383–2402) in 9.5 ml (2.8 equivalents; 94.4 mmol) of triethylamine and 95 ml of dichloromethane ($CH_2Cl_2$) is placed in a 500 ml ground-necked conical flask on which is fitted an addition funnel, and is cooled in an ice bath. After dropwise addition of 6.4 g (1.25 equivalents; 42 mmol) of phenyl chlorocarbonate dissolved in 95 ml of $CH_2Cl_2$, the mixture is stirred at 0° C. for one hour and then at room temperature for 10 hours. At the end of the reaction, the solution is washed once with saturated sodium bicarbonate ($NaHCO_3$), solution and then with water until a neutral pH is obtained, and it is dried over magnesium sulfate ($MgSO_4$). After filtration on paper and evaporation of the $CH_2Cl_2$, the residue is chromatographed on a column of silica gel, using dichloromethane as eluent. 8 g of 1,4-dibenzyl-2-phenoxycarbonyloxymethylpiperazine are thus obtained in the form of a viscous product. Yield: 57%. Rf=0.52 (2/98 v/v MeOH/$CH_2Cl_2$,).

1.2—Preparation of 1,4-dibenzyl-2-(1'-pyrrolidinocarbonyloxymethyl)piperazine 3.12 g (7,5 mmol) of 1,4-dibenzyl-2-phenoxycarbonyloxymethylpiperazine are dissolved in 9.4 ml (15 equivalents; 112.8 mmol) of pyrrolidine in a 100 ml ground-necked conical flask on which is fitted a condenser. The mixture is refluxed in a thermostatically controlled oil bath for 60 hours. After cooling and evaporation of the excess amine, the residue is taken up in $CH_2Cl_2$ and washed with water until neutral. After drying the organic phase ($MgSO_4$), filtration on paper and evaporation of the solvent, the product is chromatographed on a column of silica gel, eluting with an MeOH/$CH_2Cl_2$ mixture (0.5/99.5 v/v). 1.48 g of 1,4-dibenzyl-2-(1'-pyrrolidinocarbonyloxymethyl) piperazine are thus obtained in the form of a viscous product. Yield 50.2%. Rf=0.38 (5/95 v/v MeOH/$CH_2Cl_2$).

1.3—Preparation of 2-(1'-pyrrolidinocarbonyloxymethyl) piperazine hydrochloride 1.48 g (3.7 mmol) of 1,4-dibenzyl-2-(1'-pyrrolidinocarbonyloxymethyl)piperazine are dissolved in 40 ml of absolute ethanol and 1 ml of 12N HCl in a 100 ml ground-necked round-bottomed flask. About 100 mg of palladium (10%) on charcoal are added thereto. The mixture is then placed under a hydrogen atmosphere, vigorously stirred and gentle heating is applied (40° C.). When the initial product has disappeared (the reaction program is monitored by thin-layer chromatography eluted with an MeOH/CH$_2$Cl$_2$ mixture (5/95 v/v), after neutralization of an aliquot with a few grains of NaHCO$_3$), the solution is filtered on paper and the catalyst is rinsed several times with ethanol and water. The solvents are then evaporated off under vacuum. 1.04 g of 2-(1'-pyrrolidinocarbonyloxymethyl) piperazine hydrochloride are thus obtained and used in the following step without further purification. Yield: 98.3%. Rf=0.4 (80/20/2 v/v/v CHCl$_3$/MeOH/NH$_4$OH).

1.4—Preparation of 1,4-bis(3',4',5'-trimethoxybenzoyl)-2-(1'-pyrrolidinocarbonyloxymethyl)piperazine 1.04 g (3.63 mmol) of 2-(1'-pyrrolidinocarbonyloxymethyl)piperazine hydrochloride are dissolved in 3 ml (12.4 equivalents; 40.85 mmol) of triethylamine and 50 ml of CH$_2$Cl$_2$ in a 100 ml ground-necked conical flask on which is fitted an addition funnel. 2.88 g (3.8 equivalents; 12.5 mmol) of 3,4,5-trimethoxybenzoyl chloride dissolved in 30 ml of dry CH$_2$Cl$_2$ are added dropwise quickly. After stirring for 3 hours and addition of a few ml of ethanol, the solution is washed twice with water, dried (MgSO$_4$), filtered on paper and evaporated under vacuum. The residue is then chromatographed on a column of silica gel, eluting with an MeOH/CH$_2$Cl$_2$ mixture (1/99 v/v). The product obtained is taken up in CH$_2$Cl$_2$, washed with saturated NaHCO$_3$ solution to remove the traces of trimethoxybenzoic acid and, after evaporation of the solvents, is crystallized from a methanol/ether mixture (5/95 v/v). 591 mg of crystals of 1,4-bis(3',4',5'-trimethoxybenzoyl)-2-(1'-pyrrolidinocarbonyloxymethyl)piperazine are thus obtained after filtration on a sinter funnel, washing with ether and drying. Yield: 29%. Rf=0.43 (5/95 v/v MeOH/CH$_2$Cl$_2$). Melting point: 145.1° C.

IR: 1694 (carbamate C=O), 1622 (amide C=O), 1584 (aromatic C=C) cm$^{-1}$.

$^1$H NMR (200 MHz, CDCl$_3$, HMDS) δ in ppm: 6.57 (s, 4H, aromatic Hs), 5–4.07 (m, 5H, CH$_2$OCO and piperazine CH$_2$ and CH), 3.8 (broad s, 18H, CH$_3$O), 3.62–2.3 (m, 8H, CH$_2$N), 1.72 (broad s, 4H, pyrrolidine CH$_2$).

Example 2

Preparation of 1,4-bis(3',4',5'-trimethoxybenzoyl)-2-(N,N-diethylaminocarbonyloxymethyl)piperazine

[derivative of specific formula (I-a) in which A and B=C=O, R$_1$ to R$_6$=OCH$_3$, X=O(C=O) and Y=N(CH$_2$CH$_3$)$_2$]

2.1—Preparation of 1,4-dibenzyl-2-(N,N-diethylaminocarbonyloxymethyl)piperazine

Working according to a protocol identical to the one used in step 1.1 of Example 1, followed by treating, under the same conditions as those of step 1.2 of Example 1, 1,4-dibenzyl-2-phenoxycarbonyloxymethylpiperazine with 10 ml of diethylamine, and starting with 3 g of 1,4-dibenzyl-2-phenoxycarbonyloxymethylpiperazine, 1.75 g of 1,4-dibenzyl-2-(N,N-diethylaminocarbonyloxymethyl) piperazine are obtained in the form of a viscous product. Yield: 61.7%. Rf=0.2 (50/50 v/v ether/petroleum ether).

2.2—Preparation of 1,4-bis(3',4',5'-trimethoxybenzoyl)-2-(N,N-diethylaminocarbonyloxymethyl)piperazine Working again according to a protocol identical to the one used in step 1.3 of Example 1, followed by treating, under the same conditions as those of step 1.4 of Example 1, 0.5 g (1.73 mmol) of 2-(N,N-diethylaminocarbonyloxymethyl) piperazine hydrochloride with 1 g of 3,4,5-trimethoxybenzoyl chloride, 0.83 g of 1,4-bis(3',4',5'-trimethoxybenzoyl)-2-(N,N-diethylaminocarbonyloxymethyl)piperazine is obtained. Yield: 80%. Melting point: 128.6° C. Rf=0.35 (3/97 v/v MeOH/CH$_2$Cl$_2$).

IR: 1694 (carbamate C=O), 1632 (amide C=O), 1584 (aromatic C=C) cm$^{-1}$.

$^1$H NMR (80 MHz, CDCl$_3$, HMDS) δ in ppm: 6.62 (s, 4H, aromatic Hs), 5–4.07 (m, 5H, CH$_2$OCO and piperazine CH$_2$ and CH), 3.8 (broad s, 18H, CH$_3$O), 3.62–2.92 (m, 8H, CH$_2$N), 1.0 (t, 6H, CH$_3$).

Example 3

Preparation of 1,4-bis(3',4',5'-trimethoxybenzoyl)-2-(N,N-dipropylaminocarbonyloxymethyl)piperazine

[derivative of specific formula (I-a) in which A and B=C=O, R$_1$ to R$_6$=OCH$_3$, X=O(C=O) and Y=N(CH$_2$CH$_2$CH$_3$)$_2$]

3.1—Preparation of 1,4-dibenzyl-2-(N,N-dipropylaminocarbonyloxymethyl)piperazine Working again according to a protocol identical to the one used in step 1.1 of Example 1, followed by treating, under the same conditions as those of step 1.2 of Example 1, 3 g (27.2 mmol) of 1,4-dibenzyl-2-phenoxycarbonyloxymethyl) piperazine with 10 ml of dipropylamine, 2.28 g of 1,4-dibenzyl-2-(N,N-dipropylaminocarbonyloxymethyl) piperazine are obtained in the form of viscous product. Yield: 75%. Rf=0.22 (50/50 v/v ether/petroleum ether).

3.2—Preparation of 1,4-bis(3',4',5'-trimethoxybenzoyl)-2-(N,N-dipropylaminocarbonyloxymethyl)piperazine Working again according to a protocol identical to the one used in step 1.3 of Example 1, followed by treating, under the same conditions as those of step 1.4 of Example 1, 0.8 g of 2-(N,N-propylaminocarbonyloxymethyl)piperazine hydrochloride with 1.47 g of 3,4,5-trimethoxybenzoyl chloride, 1.24 g of 1,4-bis(3',4',5'-trimethoxybenzoyl)-2-(N,N-dipropylaminocarbonyloxymethyl)piperazine are obtained. Yield: 78%. Melting point: 109.3° C. Rf=0.36 (3/97 v/v MeOH/CH$_2$Cl$_2$).

IR: 1700 (carbamate C=O), 1640 (amide C=O), 1590 (aromatic C=C) cm$^{-1}$.

$^1$H NMR (80 MHz, CDCl$_3$, HMDS) δ in ppm: 6.62 (s, 4H, aromatic Hs), 5–4.07 (m, 5H, CH$_2$OCO and piperazine CH$_2$ and CH), 3.8 (broad s, 18H, CH$_3$O), 3.62–2.92 (m, 8H, CH$_2$N), 1.3 (m, 4H, CH$_2$), 0.8 (t, 6H, CH$_3$).

Example 4

Preparation of 1,4-bis(3',4',5'-trimethoxybenzoyl-2-(1'-piperidinocarbonyloxymethyl)piperazine

[derivative of specific formula (I-a) in which A and B=C=O, R$_1$ to R$_6$=OCH$_3$, X=O(C=O) and Y=piperidyl]

4.1—Preparation of 1,4-dibenzyl-2-(1'-piperidinocarbonyloxymethyl)piperazine

Working again according to a protocol identical to the one used in step 1.1 of Example 1, followed by treating, under the same conditions as those of step 1.2 of Example 1, 1 g of 1,4-dibenzyl-2-phenoxycarbonyloxymethylpiperazine with 10 ml de piperidine, 0.68 g of 1,4-dibenzyl-2-(1'-piperidinocarbonyloxymethyl)piperazine is obtained in the form of a viscous product. Yield: 66.5%. Rf=0.09 (70/30 v/v ether/petroleum ether).

4.2—Preparation of 1,4-bis(3',4',5'-trimethoxybenzoyl)-2-(1-piperidinocarbonyloxymethyl)piperazine Working again according to a protocol identical to the one used in step 1.3 of Example 1, followed by treating, under the same conditions as those of step 1.4 of Example 1, 0.5 g of 2-(1'-piperidinocarbonyloxymethyl)piperazine hydrochloride with 1.1 g of 3,4,5-trimethoxybenzoyl chloride, 0.8 g of 1,4-bis(3',4',5'-trimethoxybenzoyl)-2-(1'-piperidinocarbonyloxymethyl)piperazine is obtained. Yield: 56%. Melting point: 146.7° C.

IR: 1694 (carbamate C=O), 1622 (amide C=O), 1584 (aromatic C=C) cm$^{-1}$.

$^1$H NMR (200 MHz, CDCl$_3$, HMDS) δ in ppm: 6.56 (s, 4H, aromatic Hs), 5.3–4 (m, 5H, CH$_2$OCO and piperazine CH$_2$ and CH), 3.8 (broad s, 18H, CH$_3$O), 3.60–2.70 (m, 8H, CH$_2$N), 1.43 (m, 6H, piperidine CH$_2$).

Example 5

Preparation of 1,4-bis(3',4'-dimethoxybenzoyl)-2-(N,N-diethylaminocarbonyloxymethyl)piperazine

[derivative of specific formula (I-a) in which A and B=C=O, R$_1$, R$_2$, R$_4$ and R$_5$=OCH$_3$, R$_3$ and R$_6$=H, X=O (C=O) and Y=N(CH$_2$CH$_3$)$_2$]

Working again according to a protocol identical to the one used in step 1.3 of Example 1, followed by treating, under the same conditions as those of step 1.4 of Example 1, 3.36 g (11.6 mmol) of 2-(N,N-diethylaminocarbonyloxymethyl)piperazine hydrochloride with 5.8 g (2.5 equivalents—29 mmol) of 3,4-dimethoxybenzoyl chloride, and after reaction for 4 hours and chromatography on a column of silica gel eluted with an MeOH/CH$_2$Cl$_2$ mixture (1/99 v/v), 3.35 g of 1,4-bis(3',4'-dimethoxybenzoyl)-2-(N,N-diethylaminocarbonyloxymethyl)piperazine are obtained. Yield: 53.2%. Melting point: 103.9° C. Rf=0.49 (5/95 v/v MeOH/CH$_2$Cl$_2$).

IR: 1694 (carbamate C=O), 1622 (amide C=O), 1584 (aromatic C=C) cm$^{-1}$.

$^1$H NMR (200 MHz, CDCl$_3$, HMDS) δ in ppm: 6.94 (s, 2H, aromatic Hs), 6.85 (dd, 4H, aromatic Hs), 5.1–3.9 (m, 5H, CH$_2$OCO and piperazine CH$_2$ and CH), 3,8 (broad s, 12H, CH$_3$O), 3.9–2.7 (m, 8H, CH$_2$N), 1.3–0.7 (m, 6H, CH$_3$).

Example 6

Preparation of 1,4-bis(3',4',5'-trimethoxybenzoyl)-2-(isopropyloxycarbonylaminomethyl)piperazine

[derivative of specific formula (1-a) in which A and B=C=O, R$_1$ to R$_6$=OCH$_3$, X=NH(C=O)O and Y=CH(CH$_3$)$_2$]

6.1—Preparation of 1,4-dibenzyl-2-cyanopiperazine 25 g (117 mmol) of 2,3-dibromopropionitrile are dissolved in 300 ml of benzene and 100 ml of triethylamine in a ground-necked conical flask on which is fitted a condenser, and heated to 40° C. 28.17 g (117 mmol) of N,N'-dibenzylethylenediamine dissolved in 100 ml of benzene and heated to 80° C. are added dropwise thereto and the mixture is stirred for 3 hours at 80° C. After cooling, the triethylammonium hydrobromide is filtered off. The solvents (benzene and excess triethylamine) are evaporated off and the residue is taken up in ether and washed with saturated NaHCO$_3$ solution and then with water to neutral pH. The organic phase is dried (MgSO$_4$), filtered and evaporated. A viscous compound is obtained, which crystallizes in an ether/hexane mixture (60/40 v/v) in the form of 28 g of white crystals of 1,4-dibenzyl-2-cyanopiperazine. Yield: 82%. Melting point: 61.7° C. Rf=0.8 (5/95 v/v MeOH/CH$_2$Cl$_2$).

6.2—Preparation of 1,4-dibenzyl-2-aminomethylpiperazine 28 g (95 mmol) of 1,4-dibenzyl-2-cyanopiperazine are dissolved in 300 ml of ether in a 1 liter ground-necked conical flask and added dropwise to a stirred suspension of 10.96 g (3 equivalents; 284 mmol) of LiAlH$_4$ in 50 ml of ether. The mixture is kept stirring for 12 hours at room temperature. At the end of the reaction, it is hydrolyzed by dropwise addition of 20% sodium hydroxide solution. The solid aluminum hydroxide complex formed is separated out by settling and rinsed with ether. The ether phase is washed with water, dried (MgSO$_4$), filtered and evaporated and the residue obtained is purified by chromatography on a column of silica gel, eluting with an MeOH/CH$_2$Cl$_2$ mixture (1/99 v/v). 22 g of 1,4-dibenzyl-2-aminomethylpiperazine are thus recovered in the form of a viscous product. Yield: 77.5%. Rf=0.2 (80/20 v/v CH$_2$Cl$_2$/MeOH).

6.3—Preparation of 1,4-dibenzyl-2-isopropyloxycarbonylaminomethylpiperazine and its hydrochloride 22 g (75 mmol) of 1,4-dibenzyl-2-aminomethylpiperazine dissolved in 300 ml of toluene are mixed with 100 ml of triethylamine in a ground-necked conical flask. 97 ml (0.1 mol) of isopropyl chloroformate, taken up by syringe, are dissolved in 50 ml of toluene, and are then added dropwise to the above solution. At the end of the addition, the mixture is stirred for 2 hours at room temperature. The solution is diluted with ether, washed with saturated NaHCO$_3$ solution and then with water to obtain a neutral pH. The organic phase is dried (MgSO$_4$), filtered and evaporated to give 28.3 g of 1,4-dibenzyl-2-isopropyloxycarbonylaminomethylpiperazine in the form of a viscous compound. Yield: 99.6%. Rf=0.4 (95/5 v/v CH$_2$Cl$_2$/MeOH).

The hydrochloride of the 1,4-dibenzyl-2-isopropyloxycarbonylaminomethylpiperazine is prepared by dissolving it in ethanol and saturating the solution with gaseous HCl. After evaporation of the ethanol, 32.3 g of 1,4-dibenzyl-2-isopropyloxycarbonylaminomethylpiperazine hydrochloride are obtained, which are used in the next step without further purification.

6.4—Preparation of 2-isopropyloxycarbonylaminomethylpiperazine hydrochloride 32.3 g (71 mmol) of 1,4-dibenzyl-2-isopropyloxycarbonylaminomethylpiperazine hydrochloride are dissolved in 100 ml of acetic acid and 200 mg of palladium (10%) on charcoal are added. Using PARR apparatus, the suspension is stirred and heated at 60° C. under hydrogen pressure (2.7 bar) overnight. The catalyst is filtered off and the solvent is evaporated to give a compound which is crystallized from an ethanol/ether mixture (5/95 v/v) to give 17 g of 2-isopropyloxycarbonylaminomethylpiperazine hydrochloride in the form of white crystals. Yield: 87%. Melting point: 237.1° C. Rf=0.6 (80/20/2 v/v/v CHCl$_3$/MeOH/NH$_4$OH).

6.5—Preparation 1,4-bis(3',4',5'-trimethoxybenzoyl)-2-(isopropyloxycarbonylaminomethyl)piperazine 17 g (60 mmol) of 2-isopropyloxycarbonyl-aminomethylpiperazine hydrochloride are dissolved in 300 ml of dichloromethane and 50 ml of triethylamine in a 1 liter conical flask. 31.5 g (114 mmol) of 3,4,5-trimethoxybenzoyl chloride dissolved in 150 ml of CH$_2$Cl$_2$ are added dropwise using an addition funnel. The mixture is stirred for 3 hours. The solution is then washed with saturated NaHCO$_3$ solution and then with water until a neutral pH is obtained. The organic phase is dried (MgSO$_4$), filtered and evaporated under reduced pressure and the residue is purified on a column of silica gel, using an MeOH/CH$_2$Cl$_2$ mixture (1/99 v/v) as eluent. 26.3 g of 1,4-bis(3',4',5'-trimethoxybenzoyl)-2-(isopropyloxycarbonylaminomethyl)piperazine are thus obtained after recrystallization from an acetone/petroleum ether mixture (70/30 v/v). Yield: 72%. Melting point: 140.2° C. Rf=0.3 (95/5 v/v CH$_2$Cl$_2$/MeOH).

IR: 3368 (N—H), 1717 (carbamate C=O), 1622 (amide C=O), 1584 (aromatic C=C) cm$^{-1}$.

$^1$H NMR: (200 MHz, CDCl$_3$, HMDS) δ in ppm: 6.59 (s, 4H, aromatic Hs), 5.15 (multiplet, 1H, NH), 4.85 (quartet, 1H, piperazine CH), 4.5–4 (m, 3H, CHOCO and CH$_2$NCOO), 3.8 (broad s, 18H, CH$_3$O), 3.6–2.9 (m, 6H, CH$_2$N), 1.15 (m, 6H, CH$_3$).

Example 7

Preparation of 1,4-bis(3',4',5'-trimethoxybenzoyl-2-(tert-butylcarbonylaminomethyl)piperazine

[derivative of specific formula (I-a) in which A and B=C=O, R$_1$ to R$_6$=OCH$_3$, X=NH(C=O) and Y=C(CH$_3$)$_3$]

7.1—Preparation of 1,4-dibenzyl-2-tert-butylcarbonylaminomethylpiperazine 3.36 g (13.1 mmol) of 1,4-dibenzyl-2-aminomethylpiperazine prepared according to a protocol identical to the one used in steps 6.1 and 6.2 of Example 6 are dissolved in 5.5 ml (3 equivalents; 39.3 mmol) of triethylamine and 100 ml of dichloromethane and are treated by rapid dropwise addition of 2.63 ml (1.5 equivalents; 19.6 mmol) of 2,2-dimethylpropanoyl chloride dissolved in 30 ml of CH$_2$Cl$_2$. The solution is refluxed for 4 hours. A few ml of ethanol are then added, after which the solution is washed twice with water, once with saturated NaHCO$_3$ solution and then with water until a neutral pH is obtained. After drying the organic phase (MgSO$_4$), filtration on paper and evaporation of the solvents, the residue is chromatographed on a column of silica gel, eluting with an MeOH/CH$_2$Cl$_2$ mixture (0.5/99.5 v/v). 2.44 g of 1,4-dibenzyl-2-tert-butylcarbonylaminomethylpiperazine are thus obtained in the form of a viscous product. Yield: 49%. Rf=0.36 (95/5 v/v CH$_2$Cl$_2$/MeOH).

7.2—Preparation of 2-tert-butylcarbonylaminomethylpiperazine hydrochloride 2.44 g (6.43 mmol) of 1,4-dibenzyl-2-tert-butylcarbonylaminomethylpiperazine are dissolved in 50 ml of ethanol and 1 ml of 12N HCl in a 100-ml ground-necked round-bottomed flask. About 100 mg of palladium (10%) on charcoal are added thereto. The mixture is then placed under a hydrogen atmosphere, stirred vigorously and heated gently (40° C.) for 3 hours. The suspension is filtered on paper and the catalyst is rinsed several times with ethanol and water. The solvents are evaporated off to give 1.2 g of 2-tert-butylcarbonylaminomethylpiperazine hydrochloride. Yield: 68.6%. Melting point: 278.6° C. Rf=0.13 (80/20/[lacuna] v/v/v CHCl$_3$/MeOH/NH$_4$)OH).

7.3—Preparation of 1,4-bis(3',4',5'-trimethoxybenzoyl)-2-tert-butylcarbonylaminomethylpiperazine Working according to the protocol described in step 6.5 of Example 6, but starting with 1.2 g (4.4 mmol) of 2-tert-butylcarbonylaminomethylpiperazine and 2.33 g (2.3 equivalents; 10.1 mmol) of 3,4,5-trimethoxybenzoyl chloride, 900 mg of 1,4-bis(3',4',5'-trimethoxybenzoyl)-2-tert-butylcarbonylaminomethylpiperazine are obtained, after reaction for 24 hours at room temperature and chromatography on a column of silica gel eluted with an MeOH/CH$_2$Cl$_2$ mixture (2/98 v/v). Yield: 34.6%. Rf=0.29 (95/5 v/v CH$_2$Cl$_2$/MeOH). Melting point: 146.5° C.

Example 8

Preparation of 1-benzyl-4-(3',4',5'-trimethoxybenzoyl)-2-(N,N-diethylaminocarbonyloxymethyl)piperazine hydrochloride

[derivative of specific formula (I-b) in which R$_4$ to R$_6$=OCH$_3$, R$_8$=H, X=O(C=O) and Y=N(CH$_2$CH$_3$)$_2$]

8.1—Preparation of 4-(3',4',5'-trimethoxybenzoyl)-2-(N,N-diethylaminocarbonyloxymethyl)piperazine 19.86 g (86 mmol) of 2-(N,N-diethylaminocarbonyloxymethyl)piperazine dihydrochloride prepared in accordance with step 2.2 of Example 2 are dissolved in 400 ml of CH$_2$Cl$_2$ and 42 ml (3.5 equivalents) of triethylamine in a 1 liter ground-necked conical flask on which is fitted an addition funnel, and which is immersed in an ice bath. A solution containing 19.83 g (86 mmol) of 3,4,5-trimethoxybenzoyl chloride in 200 ml of CH$_2$Cl$_2$ is added dropwise to the solution thus obtained. The reaction is monitored by thin-layer chromatography, using a CH$_2$Cl$_2$/MeOH/NH$_4$OH mixture (80/20/0.5 v/v/v) as eluent, until the starting amine has disappeared. The solution is then washed with saturated NaHCO$_3$ solution and then with water until a neutral pH is obtained. The organic phase is then dried (MgSO$_4$), filtered and evaporated and the residue obtained is chromatographed on a column of silica gel with an MeOH/CH$_2$Cl$_2$ mixture (1/99 v/v) as eluent. 18.75 g of 4-(3',4',5'-trimethoxybenzoyl)-2-(N,N-diethylaminocarbonyloxymethyl)piperazine are thus obtained in the form of a viscous oil. Yield: 53.33%.

8.2—Preparation of 1-benzyl-4-(3',4',5'-trimethoxybenzoyl)-2-(N,N-diethylaminocarbonyloxymethyl)piperazine hydrochloride 20.8 g (51 mmol) of 4-(3',4',5'-trimethoxybenzoyl)-2-(N,N-diethylaminocarbonyloxymethyl)piperazine, 7.74 g (61 mmol) of benzyl chloride, 200 ml of acetonitrile, 10 g of potassium carbonate (K$_2$CO$_3$) and 1 g of potassium iodide (KI) are introduced into a 500 ml ground-necked conical flask. The mixture is refluxed for 2 hours. The suspension obtained is filtered on a sinter funnel and the solid thus recovered is washed with acetone. The filtrate is evaporated and is then taken up with CH$_2$Cl$_2$ and washed with water. The organic phase is dried (MgSO$_4$), filtered and evaporated and the residue obtained, purified on a column of silica gel eluted with an MeOH/CH$_2$Cl$_2$ mixture (2/98 v/v), gives a product which is redissolved in absolute ethanol and converted to the hydrochloride by bubbling a stream of gaseous HCl through. After evaporation of the ethanol, the hydrochloride thus formed is crystallized from an acetone/ether mixture (60/40 v/v), to give 26.46 g of crystals of 1-benzyl-4-(3',4',5'-trimethoxybenzoyl)-2-(N,N-diethylaminocarbonyloxymethyl)piperazine hydrochloride. Yield: 96.9%. Melting point: 134° C.

IR: 1690 (carbamate C=O), 1631 (amide C=O), 1586 (aromatic C=C) cm$^1$.

$^1$H NMR (200 MHz, CDCl$_3$, HMDS) δ in ppm: 13.38 (multiplet, 1H, HCl), 7.58–7.39 (2 broad s, 5H, aromatic benzyl Hs), 6.55 (s, 2H, aromatic Hs), 5.15–3.9 (m, 7H, CH$_2$OCO, benzyl CH$_2$ and piperazine CH$_2$ and CH), 3.78 (broad s, 9H, CH$_3$0), 3.6–2.1 (m, 8H, CH$_2$N), 1.05 (t, 6H, CH$_3$).

Example 9

Preparation of 1-diphenylmethyl-4-(3',4',5'-trimethoxybenzoyl)-2-(N,N-diethylaminocarbonyloxymethyl)piperazine hydrochloride

[derivative of specific formula (I-b) in which R$_4$ to R$_6$=OCH$_3$, R$_8$=phenyl, X=O(C=O) and Y=N(CH$_2$CH$_3$)$_2$]

300 mg (0.67 mmol) of 4-(3',4',5'-trimethoxybenzoyl)-2-(N,N-diethylaminocarbonyloxymethyl)piperazine prepared in accordance with step 8.1 of Example 8, 320 mg (2 equivalents) of diphenylmethyl bromide, 60 mg (0.5 equivalent) of potassium iodide and 560 mg (6 equivalents) of potassium carbonate are stirred at reflux in 10 ml of acetontrile for 60 hours in a 50-ml ground-necked conical flask on which is fitted a condenser and which is placed in an oil bath. The suspension is then filtered on paper and the salts collected are rinsed several times with acetonitrile. The filtrate is evaporated and the residue is taken up in $CH_2Cl_2$ and washed successively with saturated $NaHCO_3$ and water until a neutral pH is obtained. Chromatography on a column of silica gel, eluting with an $MeOH/CH_2Cl_2$ mixture (0.5/99.5 v/v) makes it possible to isolate a product which is redissolved in absolute ethanol and converted to the hydrochloride by bubbling a stream of gaseous HCl through. The addition of ether causes 90 mg of 1-diphenylmethyl-4-(3',4',5'-trimethoxybenzoyl)-2-(N,N-diethylaminocarbonyloxymethyl)piperazine hydrochloride to precipitate. Yield: 22%. Melting point: 189.5° C.

IR: 3349 ($N^+$-H), 1694 (carbamate C=O), 1623 (amide C=O), 1580 (aromatic C=C) $cm^{-1}$.

$^1$H NMR: (200 MHz, $CDCl_3$, HMDS) δ in ppm: 7.9 (dd, 4H, ortho H of the phenyls), 7.3 (m, 6H, aromatic Hs), 6,55 (s, 2H, aromatic Hs), 5.06 (s, 1H, CH of the diphenylmethyl), 4.6 and 3.2 (2m, 13H, $CH_2OCO$, piperazine $CH_2$ and CH), 3.78 (broad s, 9 H, $CH_3O$), 0.8 (m, 6H, $CH_3$).

Example 10

Preparation of 1-(3',4',5'-trimethoxybenzoyl)-4-benzyl-2-(N,N-diethylaminocarbonyloxymethyl)piperazine hydrochloride

[derivative of specific formula (I-c) in which $R_1$ to $R_3$=$OCH_3$, $R_8$=H, X=O(C=O) and Y=N$(CH_2CH_3)_2$]

10.1—Preparation of 4-triphenylmethyl-2-(N,N-diethylaminocarbonyloxymethyl)piperazine A solution comprising 24.68 g (86 mmol) of 2-(N,N-diethylaminocarbonyloxymethyl)piperazine hydrochloride prepared according to a protocol identical to step 1.3 of Example 1 and dissolved in 400 ml of $CH_2Cl_2$ and 42 ml (3.5 equivalents) of triethylamine in a 1 liter ground-necked conical flask is cooled to −10° C. A solution comprising 233 g (86 mmol) of triphenylmethyl chloride in 200 ml of $CH_2Cl_2$ is added dropwise over a period of about 2 hours to this solution thus cooled. After stirring for 3 hours at the same temperature, the mixture is washed with saturated $NaHCO_3$ solution and then with water until a neutral pH is obtained. After drying ($MgSO_4$), filtration and evaporation of the organic phase, 35.9 g of 4-triphenylmethyl-2-(N,N-diethylaminocarbonyloxymethyl)piperazine are obtained in the form of a viscous product. Yield: 91.6%.

10.2—Preparation of 1-(3',4',5'-trimethoxybenzoyl)-4-triphenylmethyl-2-(N,N-diethylaminocarbonyloxymethyl)piperazine 24.16 g (53 mmol) of 4-triphenylmethyl-2-(N,N-diethylaminocarbonyloxymethyl)piperazine are dissolved in 15 ml (2 equivalents) of triethylamine and 100 ml of $CH_2Cl_2$, in a 500 ml ground-necked conical flask on which is fitted an addition funnel, and which is placed in an ice bath. A solution comprising 14.6 g (1.2 equivalents) of 3,4,5-trimethoxybenzoyl chloride in 25 ml of $CH_2Cl_2$ is added dropwise to the solution thus obtained. The reaction is monitored by thin-layer chromatography using ether as eluent and, when the reaction is complete, the mixture is washed with saturated $NaHCO_3$ solution and then with water until a neutral pH is obtained. The residue obtained after drying ($MgSO_4$), filtration and evaporation of the solvent consists of 32.32 g of 1-(3',4',5'-trimethoxybenzoyl)-4-triphenylmethyl-2-(N,N-diethylaminocarbonyloxymethyl)piperazine, this product being used in the next step without further purification. Yield: 93.4%.

10.3—Preparation of 1-(3',4',5'-trimethoxybenzoyl)-2-(N,N-diethylaminocarbonyloxymethyl)piperazine 26.77 g (41 mmol) of 1-(3',4',5'-trimethoxybenzoyl)-4-triphenylmethyl-2-(N,N-diethylaminocarbonyloxymethyl)piperazine are dissolved in 200 ml of methanol in a 500 ml ground-necked round-bottomed flask and are converted to the hydrochloride by bubbling a stream of gaseous HCl through under cold conditions, followed by stirring at room temperature until the starting material has completely disappeared. After evaporating off the methanol, the residue is taken up in $CH_2Cl_2$ and washed with saturated $NaHCO_3$ solution and then with water until a neutral pH is obtained. After drying ($MgSO_4$), filtration and evaporation of the organic phase, a chromatography on a column of silica gel, eluting with $CH_2Cl_2$, gives 12.54 g of 1-(31,4',5'-trimethoxybenzoyl)-2-(N,N-diethylaminocarbonyloxymethyl)piperazine in the form of a viscous product. Yield: 74.8%.

10.4—Preparation of 1-(3',4',5'-trimethoxybenzoyl)-4-benzyl-2-(N,N-diethylaminocarbonyloxymethyl)piperazine hydrochloride Working according to a protocol identical to the one used in step 8.2 of Example 8, and starting with 10.63 g (26 mmol) of 1-(3',4',5'-trimethoxybenzoyl)-2-(N,N-diethylaminocarbonyloxymethyl)piperazine, 11,55 g of 1-(3',4',5'-trimethoxybenzoyl)-4-benzyl-2-(N,N-diethylaminocarbonyloxymethyl)piperazine hydrochloride are obtained. Yield: 83%. Melting point: 180.6° C.

The infrared (IR) and nuclear magnetic resonance (NMR) spectral characteristics of this compound are identical to those of the 1-benzyl-4-(3',4',5'-trimethoxybenzoyl)-2-(N,N-diethylaminocarbonyloxymethyl)piperazine hydrochloride of which it represents the isomer.

Example 11

Preparation of 1-(3',4',5'-trimethoxybenzoyl)-4-(3',4',5'-trimethoxythiobenzoyl)-2-(N,N-diethylaminocarbonyloxymethyl)piperazine

[derivative of specific formula (I-a) in which A=C=O, B=C=S, $R_1$ to $R_6$=$OCH_3$, X=O(C=O) and Y=N$(CH_2CH_3)_2$]

11.1—Preparation of 4-(3',4',5'-trimethoxythiobenzoyl)-2-(N,N-diethylaminocarbonyloxymethyl)piperazine 1.7 g (3.66 mmol) of 4-(3',4',5'-trimethoxybenzoyl)-2-(N,N-diethylaminocarbonyloxymethyl)piperazine, prepared according to the protocol described in step 8.1 of Example 8, are dissolved in 34 ml of THF and cooled in an ice bath. 1.7 g (1 equivalent) of Lawesson's reagent are added portionwise thereto. The solution is stirred at 0° C. for 30 minutes and then at room temperature overnight. The solvent is then removed under vacuum and the residue is rapidly purified on a column of silica gel (eluents: $CH_2Cl_2$ and then 1% MeOH in $CH_2Cl_2$) to give 1.1 g of 4-(3',4',5'-trimethoxythiobenzoyl)-2-(N,N-diethylaminocarbonyloxymethyl)piperazine in the form of a viscous yellow product. Yield: 62.4%.

IR: 3314 (NH), 2967 (CH), 2836 ($CH_3O$), 1696 (carbamate C=O), 1582 (aromatic C=C) $cm^{-1}$.

11.2—Preparation of 1-(3',4',5'-trimethoxybenzoyl)-4-(3',4',5'-trimethoxythiobenzoyl)-2-(N,N-diethylaminocarbonyloxymethyl)piperazine 250 mg (0.6 mmol) of 4-(3',4',5'-trimethoxybenzoyl)-2-(N,N-diethylaminocarbonyloxymethyl)piperazine, 164 µl (2 equivalents) of $Et_3N$ and 200 mg (1.5 equivalents) of 3,4,5-trimethoxybenzoyl chloride are dissolved in 10 ml of $CH_2Cl_2$ in a 25 ml round-bottomed flask on which is fitted a $CaCl_2$ guard tube, and the mixture is stirred at room temperature overnight. The solution is then washed with water (2×10 ml), dried, filtered and evaporated. The residue is then purified on a column of silica gel (eluting with 1% MeOH in $CH_2Cl_2$) and crystallized from an MeOH/diethyl ether/hexane mixture to give 150 mg of 1-(3',4',5'-trimethoxybenzoyl)-4-(3',4',5'-trimethoxythiobenzoyl)-2-(N,N-diethylaminocarbonyloxymethyl)piperazine. Yield: 41%. Rf=0.53 (5195 v/v MeOH/$CH_2CH_2$). Melting point: 105.8° C.

IR: 2967 (CH), 2839 ($CH_3O$), 1691 (amide C=O), 1584, 1506 (aromatic C=C) $cm^{-1}$.

$^1$H NMR (200 MHz, $CDCl_3$, HMDS) δ in ppm: 6.58 (s, 2H, piperazine CH), 4.5–3.9 (m, 3H, piperazine CH, $CH_2OCO$), 3.79 (s, 18H, $CH_3O$), 3.6–2.6 (multiplet, 8H, piperazine CH, $CH_2NCO$), 1.03 (m, 6H, $CH_3$).

Example 12

Preparation of 1,4-bis(3',4',5'-trimethoxybenzol)-2-(N,N-diethylaminocarbonyloxymethylpiperazine

[derivative of specific formula (I-a) in which A and B=C=S, $R_1$ to $R_6$=$OCH_3$, X=O(C=O) and Y=N($CH_2CH_3$)$_2$]

500 mg (0.83 mmol) of 1,4-bis(3',4',5'-trimethoxybenzoyl)-2-(N,N-diethylaminocarbonyloxymethyl)piperazine prepared according to Example 2 are dissolved in 10 ml of THF and cooled in an ice bath. 670 mg (2 equivalents) of Lawesson's reagent are added portionwise thereto. The solution is maintained at 0° C. for 30 minutes and then at room temperature for 20 hours, and is refluxed for 1 hour. After cooling and evaporation of the solvent, the residue is purified on a column of silica gel (eluting with 1/99 v/v MeOH/$CH_2Cl_2$). 460 mg of 1,4-bis(3',4',5'-trimethoxybenzoyl)-2-(N,N-diethylaminocarbonyloxymethyl)piperazine are thus obtained in the form of yellow crystals. Yield: 87.3%. Melting point: 95.1 ° C.

IR: 2936 (CH), 2833 ($CH_3O$), 1700 (carbamate C=O), 1582, 1507 (aromatic C=C) $cm^{-1}$.

$^1$H NMR (200 MHz, $CDCl_3$, HMDS) δ in ppm: 7.2 (multiplet, 4H, aromatic H), 5.15 and 4.9 (2 multiplets, 2H, piperazine CH), 4.4–3.9 (multiplet, 3H, piperazine CH, $CH_2OCO$), 3.79 (s, 18H, $CH_3O$), 3.6–2.1 (m, 8H, piperazine $CH_2$, $CH_2NCO$), 0.9 (m, 6H, $CH_3$).

Example 13

Preparation of 1-(3',4',5'-trimethoxythiobenzoyl)-4-(3',4',5'-trimethoxybenzoyl)-2-(N,N-diethylaminocarbonyloxymethyl)piperazine

[derivative of specific formula (I-a) in which A=C=S, B=C=O, $R_1$ to $R_6$=$OCH_3$, X=O(C=O) and Y=N($CH_2CH_3$)$_2$]

13.1—Preparation of 1-(3',4',5'-trimethoxythiobenzoyl)-2-(N,N-diethylaminocarbonyloxymethyl)piperazine 1.4 g (3.44 mmol) of 1-(3',4',5'-trimethoxybenzoyl)-2-(N,N-diethylaminocarbonyloxymethyl)piperazine prepared according to the protocol described in steps 10.1 to 10.3 of Example 10, are dissolved in 30 ml of THF and cooled in an ice bath. 1.4 g (1 equivalent) of Lawesson's reagent are gradually added thereto. The solution is kept cold for 1 hour and then at room temperature overnight. After removal of the solvent under vacuum and rapid purification on silica gel (eluent: 1/99 v/v MeOH/$CH_2Cl_2$), 1.2 g of 1-(3',4',5'-trimethoxythiobenzoyl)-2-(N,N-diethylaminocarbonyloxymethyl)piperazine are obtained. Yield: 82%.

IR: 1690 (carbamate C=O), 1592 (aromatic C=C) $cm^{-1}$.

13.2—Preparation of 1-(3',4',5'-trimethoxythiobenzoyl)-4-(3',4',5'-trimethoxybenzoyl)-2-(N,N-diethylaminocarbonyloxymethyl)piperazine 780 mg of 3',4',5'-trimethoxybenzoyl chloride are added portionwise to a solution comprising 1.2 g (2.82 mmol) of 1-(3',4',5'-trimethoxythiobenzoyl)-2-(N,N-diethylaminocarbonyloxymethyl)piperazine and 800 µl (2 equivalents) of $Et_3N$ in 30 ml of $CH_2Cl_2$. Stirring is continued overnight at room temperature. After addition of 2 ml of EtOH, the solution is washed with 10 ml of water, dried, filtered and evaporated. The residue is then purified rapidly, eluting with a mixture of MeOH and $CH_2Cl_2$ (1/99 v/v). After crystallization from an MeOH/diethyl ether mixture, 405 mg of 1-(3',4',5'-trimethoxythiobenzoyl)-4-(3',4',5'-trimethoxybenzoyl)-2-(N,N-diethylaminocarbonyloxymethyl)piperazine are thus obtained. Yield: 23.2%. Rf=0.44 (5/95 v/v MeOH/$CH_2Cl_2$). Melting point: 175.4° C.

IR: 1699 (carbamate C=O), 1642 (amide C=O), 1588 and 1507 (aromatic C=C) $cm^{-1}$.

$^1$H NMR (200 MHz, $CDCl_3$, HMDS) δ in ppm: 6.6 (s, 2H, aromatic H), 6.6–6 (m, 2H, aromatic H), 4.9–3.9 (m, 5H, $CH_2O$, CH and $CH_2NCS$); 3.8 (s, 18H, $CH_3O$), 3.7–2. (m, 8H, $CH_2NCO$), 1,04 (broad s, 6H, $CH_3$).

II—Inhibitory Activity on HIV Replication

The inhibitory activity of the piperazine derivatives in accordance with the invention on HIV replication was established by a series of experiments designed to test in vitro:

firstly, the ability of these derivatives to inhibit HIV replication in a first experimental system using only monocyte-derived macrophage cultures (Example 14);

secondly, various procedures for treating these monocyte-derived macrophages with the piperazine derivatives in accordance with the invention (Example 15); and finally, the ability of these same derivatives to inhibit HIV replication in two other experimental systems using cultures of monocytes not differentiated into macrophages, on the one hand, and peripheral blood mononuclear cell cultures, on the other hand (Example 16). In this latter cell population, which includes the two major cellular targets of HIV, namely the macrophages and the CD4+ T lymphocytes, the various levels of cellular activation were mimicked artificially by stimulating the cells with recombinant human interleukin-2 after activation or otherwise of these cells with a mitogen, phytohemagglutinin-P.

Example 14

Inhibitory Activity in Monocyte-Derived Macrophages 14.1—Protocol a) Production and Culturing of the Macrophages The macrophages were obtained by differentiation of monocytes which were themselves isolated from peripheral blood mononuclear cells.

To do this, the peripheral blood mononuclear cells were separated from the other elements of the blood by centrifugation on a ficoll gradient (MSL 2000, from Eurobio) and washed twice in RPMI 1640 medium (from Boehringer Mannheim). The monocytes were isolated from these mononuclear cells by counter-current elutriation. The fractions collected were analyzed using a cell counter-analyzer (from Coulter) and the cells corresponding to each fraction were phenotyped and then analyzed using a flow cytometer (FACS, from Becton Dickinson). The purity of the monocytes thus collected is at least equal to 95%.

These monocytes were then suspended in a culture medium (medium A below) comprising RPMI 1640 medium (from Boehringer Mannheim) supplemented with 10% fetal calf serum (from Boehringer Mannheim) decomplemented beforehand by treatment at 56° C. for 30 minutes, L-glutamine (2 mM) and a solution containing 100 µg/ml of 3 antibiotics: penicillin, streptomycin and neomycin (PSN, from Life Technologies), at a rate of 1 million monocytes per ml of culture medium. The resulting suspension was distributed in the wells of 48-well plates, by depositing 1 ml of suspension in each well (i.e. 1 million monocytes) and the monocytes were differentiated into macrophages by leaving the monocytes to adhere to the walls of the wells for 7 days. The macrophages were then cultured for 28 days using the same culture medium as that used to differentiate them.

Throughout their differentiation and subsequent culturing, the macrophages were maintained at 37° C. in a humidity-saturated atmosphere comprising 5% $CO_2$. The culture medium in each well was renewed every three or four days, by removing the supernatants and replacing them with an equivalent volume of fresh medium.

b) Treatment of the Macrophages with the Piperazine Derivatives

The piperazine derivatives to be tested were dissolved in dimethyl sulfoxide (DMSO) at a concentration of 200 mM. The solutions thus obtained were divided into aliquots and stored at −20° C. protected from light. The dilutions required to carry out the tests were prepared at the time of use in medium A as described above.

The treatment of the macrophages with the piperazine derivatives was initiated on the third day of culture (D3)— i.e. 24 hours before infecting them with HIV (D4)—, by adding the piperazine derivatives to be tested to the culture medium. The treatment was then maintained throughout the culturing of the macrophages, i.e. up to the 28th day (D28). For each piperazine derivative, different doses corresponding to 0.01 µM, 0.1 µM, 1 µM, 10 µM and 100 µM were tested.

c) Infection of the Macrophages with HIV

The macrophages were infected with the HIV-1/Ba-L reference isolate with macrophage tropism (Gartner et al., Science, 1986, 233, 215–219), which subcultures efficiently in vitro in this cell type.

The viral stock was constituted by amplifying in vitro the constituent strain of this isolate in umbilical blood mononuclear cell cultures preactivated with phytohemagglutinin-P (PHA-P, from Difco Laboratories, 1 µg of PHA-P/ml of culture medium) and stimulated with recombinant human interleukin-2 (IL-2, from Boehringer Mannheim, 20 IU of IL-2/ml of culture medium). The supernatants of these cultures were centrifuged at 360 000×g for 5 minutes in order to remove the soluble factors such as the cytokines. The pellets were resuspended in RPMI 1640 medium and the viral stock was assayed using peripheral blood mononuclear cells preactivated with PHA-P (*Manuel des Techniques Virologiques Consensus*, published by ANRS). The infectious doses required to infect 50% of the macrophages ($ID_{50}$) were determined using the Kärber formula (Kärber et al., *Arch. Exp. Path. Pharmak.*, 1931, 162, 956–959).

The macrophages were infected by introducing into each culture well a viral load corresponding to 10 000 $ID_{50}$, i.e. a multiplicity of infection equal to 0.01 (i.e. 0.01 viral particle/macrophage). 24 hours after infecting the macrophages, the excess virus was removed by washing these macrophages with PBS.

d) Assay of the Viral Replication and Determination of the Inhibition of This Replication The viral replication in the macrophages was monitored by assaying the enzymatic activity of the reverse transcriptase (RT) in the culture supernatants every 3 or 4 days of culturing, during the replacement of these supernatants with fresh medium, according to the method described by Rey et al., *Biochem. Biophys. Res. Comm.*, 1984, 121, 126–133, and in which the activity of the reverse transcriptase is assayed by measuring the radioactivity incorporated during elongation of the complementary strand of a poly-rA synthetic matrix in the presence of an oligo-$dT_{12-18}$ primer and of a substrate labeled with a radioactive element, tritiated methylthymidine triphosphate ($^3H$ TTP).

To do this, 400 µl of supernatant contained in each of the culture wells were subjected to ultracentrifugation at 360 000×g for 5 minutes. The reverse transcriptase was released by lysing the viral pellet with 20 µl of NTE-Triton (100 mM NaCl, 10 mM Tris buffer, 1 mM EDTA, 0.1% Triton X-100). These 20 µl were then incubated with 40 µl of the following reaction mixture: 62.5 mM pH 7.8 Tris buffer, 25 mM KCl, 6.25 mM $MgCl_2$, 1.25 mM DTT, poly-rA and oligo-$dT_{12-18}$ $2.5 \times 10^{-3}$ optical density units (ODU), $5.55 \times 10^{-3}$ Tbq $^3H$ TTP. After 1 hour, the enzymatic reaction was stopped and the newly synthesized strands were precipitated over 20 minutes at 4° C. by adding 1 ml of sodium pyrophosphate, 5 µg of yeast DNA and 4 ml of 20% trichloroacetic acid. The resulting mixture was filtered using a cellulose acetate membrane (Millipore) which retains the radioactive poly-dT strands. The filter was washed with a 5% trichloroacetic acid solution, the residual water was removed by adding 25 µl of 70% ethanol and the filter was dried in an oven at 80° C. for 10 minutes. This filter was then introduced into a scintillation flask containing 8 ml of scintillation liquid and the radioactivity was determined using a scintillation counter (from Packard Bell). The activity of the reverse transcriptase is expressed in pmols of tritiated methylthymidine monophosphate ($^3H$ TMP) incorporated per hour and per ml of culture supernatant, or more simply in cpm per hour and per ml of culture supernatant.

The inhibition of the viral replication by the piperazine derivatives was determined by comparing, for each test derivative and for each test dose of this derivative, the cumulative activity of the reverse transcriptase at the end of culturing of the macrophages (D28) having been treated with this derivative, with that obtained for a "control" macrophage culture, i.e. a culture which received no treatment with a piperazine derivative.

For each macrophage culture treated, a percentage of inhibition (I) of the viral replication was thus established by means of the formula:

$$I = \frac{1 - \text{cumulative RT activity of the treated macrophage culture}}{\text{cumulative RT activity of the "control" macrophage culture}} \times 100$$

14.2—Results

FIG. 1 illustrates, by way of example and in the form of a curve, the dose-effect relationship of a piperazine derivative in accordance with the invention, namely 1,4-bis(3',4', 5'-trimethoxybenzoyl)-2-(N,N-diethylaminocarbonyloxymethyl)piperazine as obtained in Example 2, on the HIV replication in the monocyte-derived macrophages. The percentages of inhibition (I) of the viral replication obtained during the treatment of the macrophages with this derivative are expressed on the y-axis, and the doses tested, in $\mu$M, are expressed on the x-axis.

This figure shows that 1,4-bis(3',4',5'-trimethoxybenzoyl)-2-(N,N-diethylaminocarbonyloxymethyl)piperazine shows inhibitory activity on HIV replication in the monocyte-derived macrophages once it is used at doses above 1 $\mu$M and that its 50% effective dose ($ED_{50}$), i.e. the dose at which it inhibits 50% of the replication of this virus, is equal to 5 $\mu$M.

The 1-benzyl-4-(3',4',5'-trimethoxybenzoyl)-2-(N,N-diethylaminocarbonyloxymethyl)piperazine as prepared in Example 8 shows an $ED_{50}$ equal to 40 $\mu$M, while 1-(3',4', 5'-trimethoxybenzoyl)-4-benzyl-2-(N,N-diethylaminocarbonyloxymethyl)piperazine as prepared in Example 10 has an $ED_{50}$ equal to 13 $\mu$M.

Example 15

Implementation of the Various Procedures for Treating Monocyte-Derived Macrophages Various procedures for treating monocyte-derived macrophages with the piperazine derivatives in accordance with the invention were tested using a protocol similar to that described in Example 14.

In these tests, however, the macrophage cultures were divided into three groups:

a first group (group 1 below) in which the macrophages were treated with the piperazine derivatives 24 hours before being infected with HIV (i.e. on D3) and the treatment was maintained up to D28, as described in Example 14, a second group (group 2 below) in which the macrophages were treated 24 hours after having been infected with HIV (i.e. on D5) and the treatment was maintained up to D28, and a third group (group 3 below) in which the macrophages were treated 24 hours before being infected with HIV (i.e. on D3), but the treatment was not subsequently maintained.

In all cases, the piperazine derivatives were used at a dose of 100 $\mu$M and the tests were carried out in triplicate.

Table 1 below shows, by way of example, the average of the percentages of inhibition (I) of the viral replication±standard deviation obtained by treating, according to these various procedures, the macrophages with 1,4-bis(3',4',5'-trimethoxybenzoyl)-2-(N,N-diethylaminocarbonyloxymethyl)piperazine.

TABLE 1

| Groups | I |
| --- | --- |
| Group 1 | 91 ± 2 |
| Group 2 | 88 ± 12 |
| Group 3 | 73 ± 2 |

These results show that 1,4-bis(3',4',5'-trimethoxybenzoyl)-2-(N,N-diethylaminocarbonyloxymethyl)piperazine is capable of inhibiting HIV replication in monocyte-derived macrophages, whether it is administered before or after the infection of these macrophages with this virus, and that its antiviral activity endures, even in the absence of a prolonged treatment.

Example 16

Inhibitory Activity in Monocytes Not Differentiated into Macrophages and in Peripheral Blood Mononuclear Cells The ability of the piperazine derivatives to inhibit HIV replication in the monocytes not differentiated into macrophages and in the peripheral blood mononuclear cells (PBMCs) was tested using a protocol similar to that described in Example 14.

In these tests, however, the monocytes were cultured without a differentiation step.

As regards the peripheral blood mononuclear cell cultures, these were divided into three groups:

a first group (group 1 below) in which these mononuclear cells were activated during the first 48 hours of culturing with phytohemagglutinin-P, and stimulated throughout the culturing with recombinant human interleukin-2; these cultures were prepared in a culture medium (medium B below) consisting of medium A supplemented with 20 IU of IL-2/ml of culture medium and the mononuclear cells were activated with phytohemagglutinin-P by adding 1 $\mu$g of this compound per ml of culture medium;

a second group (group 2 below) in which the mononuclear cells were not activated with phytohemagglutinin-P, but were stimulated with recombinant human interleukin-2 and which were prepared in medium B; and a third group (group 3 below) in which the mononuclear cells were not subjected either to activation with phytohemagglutinin-P or to stimulation with recombinant human interleukin-2, and which were prepared in medium A.

In all cases, the treatment of the cells (monocytes and PBMCs) with the piperazine derivatives in accordance with the invention was initiated on D3—i.e. 24 hours before infecting them with HIV (D4)—, by adding the piperazine derivatives to be tested to the culture medium. The treatment was then maintained throughout the culturing of the cells, i.e. up to the 28th day (D28). Each piperazine derivative was tested at a dose of 100 $\mu$M and the tests were carried out in triplicate.

Figure 2:
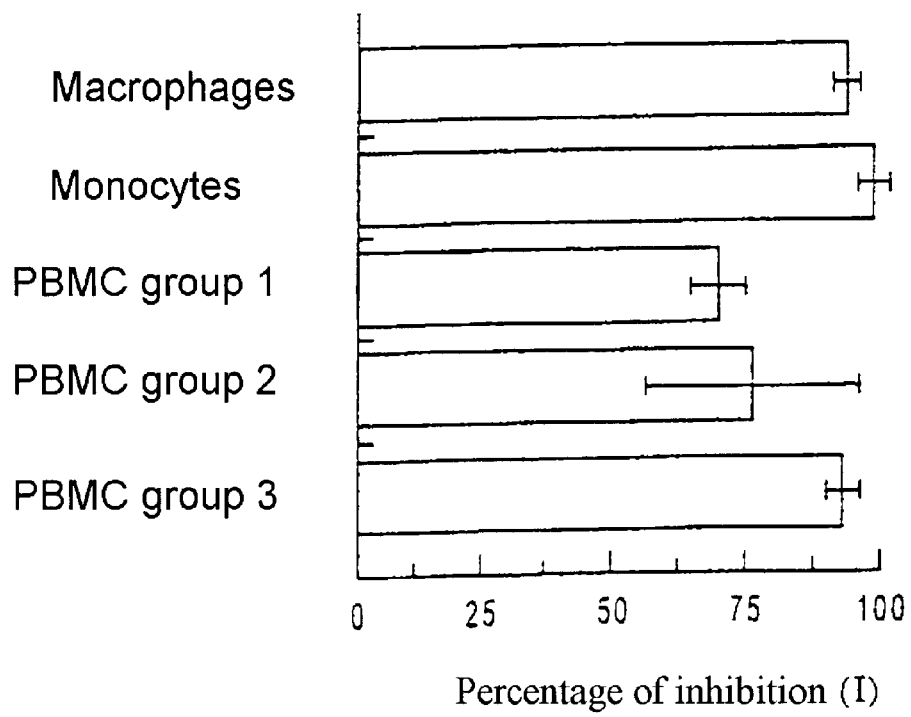
FIG. 2 illustrates, in the form of a histogram, the inhibitory activity of 1,4-bis(3',4',5'-trimethoxybenzoyl)-2-(N,N-diethylaminocarbonyloxymethyl)piperazine on HIV replication in various cell populations (monocyte-derived macrophages, monocytes and mononuclear cells from peripheral blood) at a dose of 100 $\mu$M.

FIG. 2 illustrates, by way of example and in the form of a histogram, the average of the percentages of inhibition (I) of the viral replication±standard deviation obtained by treating the monocytes and the peripheral blood mononuclear cells of groups 1, 2 and 3 with 1,4-bis(3',4',5'-trimethoxybenzoyl)-2-(N,N-diethylaminocarbonyloxymethyl)piperazine. This histogram also indicates the average of the percentages of inhibition (I) of the viral replication±standard deviation observed by treating the monocyte-derived macrophages with the same piperazine derivative and under the same conditions.

III—Cytotoxicity

The cytotoxicity of the piperazine derivatives in accordance with the invention was evaluated by measuring, by means of three different tests:

a test with Trypan blue, an MTT test or test with 3-(4,5-dimethylthiazol-2-yl)-2, 5-diphenyltetrazolium bromide, and a test with neutral red, the viability of peripheral blood mononuclear cell cultures and of monocyte-derived macrophage cultures treated with the piperazine derivatives in accordance with the invention and by comparing the results obtained with those observed for "control" cultures, i.e. peripheral blood mononuclear cell cultures or monocyte-derived macrophage cultures prepared under the same conditions but in the absence of any treatment with said piperazine derivatives.

The Trypan blue test is a test conventionally carried out on non-adherent cells and was thus used to measure the effects of the piperazine derivatives in accordance with the invention on the viability of the peripheral blood mononuclear cells. This test consists in mixing a sample of the cell suspension whose viability it is desired to test, with Trypan blue which diffuses into the dead cells but not into the live cells, and in counting the dead cells (blue cells) and the live cells (refringent cells) on a Malassez cell.

In contrast, the MTT test is conventionally carried out on adherent cells. It was thus used to measure the effects of the piperazine derivatives in accordance with the invention on the monocyte-derived macrophages. This test consists in incubating for 4 hours a sample of the cell suspension whose viability it is desired to test, in the presence of MTT. MTT, which is a yellow colored product, is metabolized by the mitochondrial dehydrogenases of the live cells into formazan, which is insoluble and violet in color. Thus, the difference in absorbance between MTT and formazan makes it possible to quantify, by spectrometry, the dehydrogenase activity of the mitochondria and, consequently, the viability of the cells present in the suspension (Schwartz et al., *AIDS Res. Hum. Retroviruses*, 1988, 4, 441–448).

The neutral red test is also a test which is used on adherent cells and which was used to measure the effects of the piperazine derivatives in accordance with the invention on the monocyte-derived macrophages. This test consists in incubating a sample of the cell suspension whose viability it is desired to test, with neutral red, which, unlike Trypan blue, diffuses into the live cells but not into the dead cells, and then in removing the excess neutral red by washing the cells, followed by lysing them (for example with glacial acetic acid at −20° C.) and in measuring the optical density, by spectrophotometry, of the resulting lysate (Montefiori et al., *J. Clin. Microbiol.*, 1988, 26, 231–235).

In all cases, the viability of the peripheral blood mononuclear cells and of the monocyte-derived macrophages was measured before culturing them, and then at each renewal of the culture media.

Figure 3:
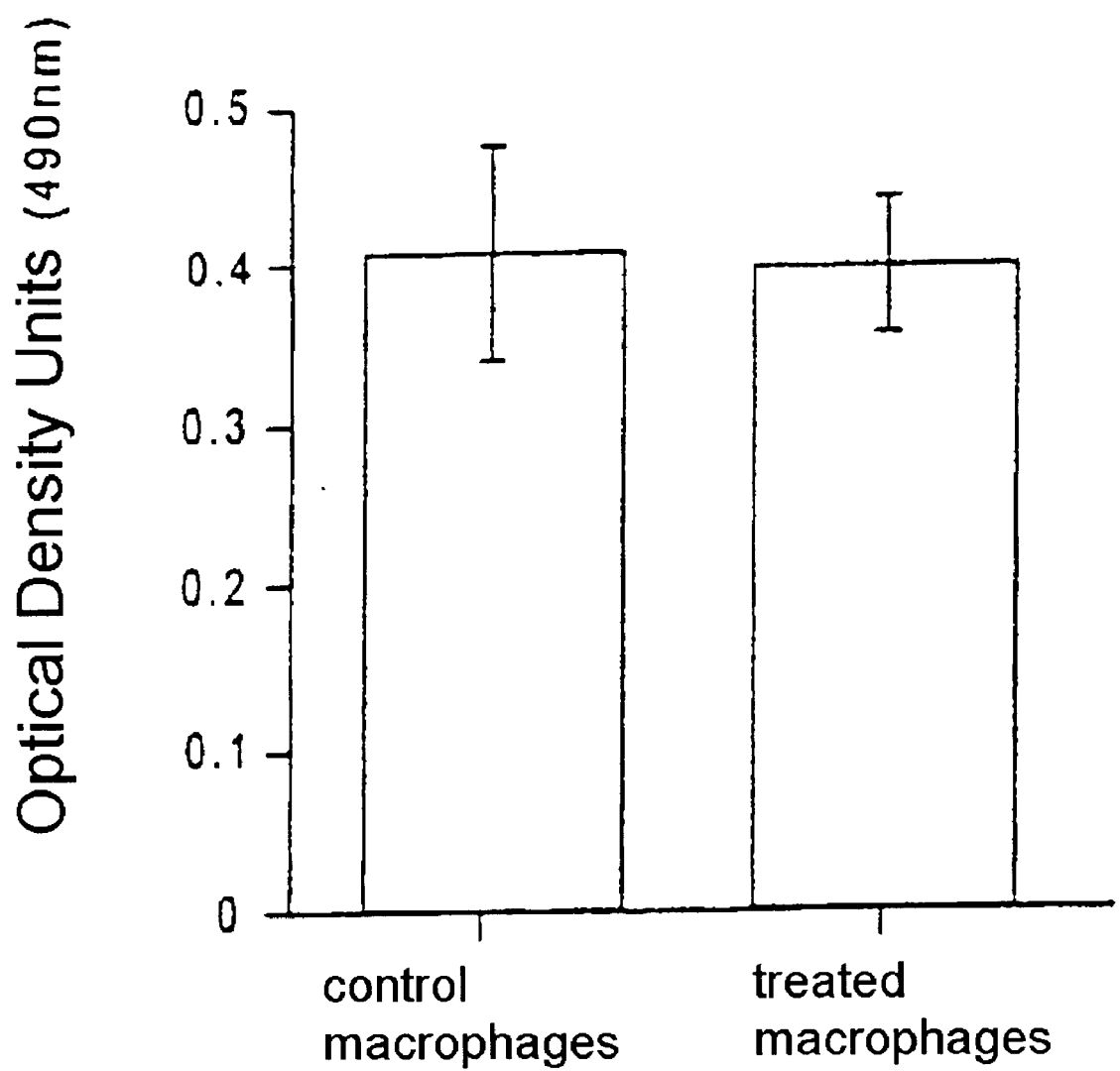
FIG. 3 illustrates, in the form of a histogram, the viability of monocyte-derived macrophages treated with 1,4-bis(3',4',5'-trimethoxybenzoyl)-2-(N,N-diethylaminocarbonyloxymethyl)piperazine at a dose of 100 $\mu$M and that of monocyte-derived macrophages not treated with this derivative.

As illustrated, by way of example, by FIG. 3 which represents, in the form of a histogram, the viability of monocyte-derived macrophage cultures treated with 1,4-bis(3',4',5'-trimethoxybenzoyl)-2-(N,N-diethylaminocarbonyloxymethyl)piperazine at a dose of 100 μM compared with that of "control" monocyte-derived macrophage cultures as measured by the neutral red test, all the viability measurements which were carried out made it possible to demonstrate an absence of cytotoxicity of the piperazine derivatives in accordance with the invention since, throughout the culturings, no significant difference is observed in the number of live cells between the cell cultures treated with these derivatives and the untreated cell cultures.

What is claimed is:

1. A method for inhibiting the replication of human immunodeficiency virus (HIV), comprising administering to an individual in need of such a teatment an inhibitory effective amount of a piperazine derivative corresponding to the general formula (I):

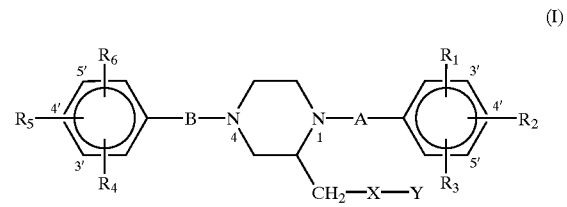

in which:
  A and B represent, independently of each other, a C=O, C=S or $CR_7R_8$ group in which $R_7$ represents a hydrogen atom or a group chosen from methyl, cyano, cyanomethyl, $CO_2CH_3$ and $(C=O)CH_3$ groups, while $R_8$ represents a hydrogen atom or a phenyl group;
  $R_1$, $R_2$, $R_3$, $R_4$, $R_5$ and $R_6$ represent, independently of each other, a hydrogen atom, a hydroxyl group or a linear or branched $C_1$–$C_5$ alkoxy group;
  X represents:
    either a group chosen from C=O, O(C=O), O(C=S), $O(SO_2)$, NH(C=O), NH(C=S), $NH(SO_2)$, S(C=O) and S(C=S) groups, in which case Y represents either a group $NR_9R_{10}$ or $CR_9R_{10}R_{11}$ in which $R_9$, $R_{10}$ and $R_{11}$ represent, independently of each other, a hydrogen atom, a linear or branched $C_1$ to $C_5$ alkyl, $C_2$ to $C_5$ alkenyl or $C_2$ to $C_5$ alkynyl group, or Y represents a nitrogen heterocycle selected from the group consisting of pyrollidino and piperidino;
    or an oxygen or sulfur atom or a group chosen from O(C=O)O, NH(C=O)O and S(C=O)O groups, in which case Y represents a group $CR_9R_{10}R_{11}$ in which $R_9$, $R_{10}$ and $R_{11}$ have the same meaning as above;
  or a pharmaceutically acceptable salt thereof.

2. A method according to claim 1, wherein $R_1$, $R_2$ and $R_3$ are borne by the carbon atoms in positions 3', 4' and 5' of the phenyl nucleus linked to the group A, while $R_4$, $R_5$ and $R_6$ are borne by the carbon atoms in positions 3', 4' and 5' of the phenyl nucleus linked to the group B.

3. A method according to claim 1, wherein the piperazine derivative corresponds to the specific formula (I-a):

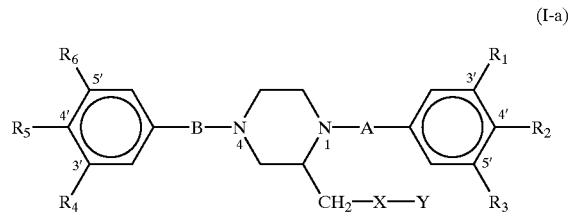

in which A and B represent, independently of each other, a C=O or C=S group, while $R_1$, $R_2$, $R_3$, $R_4$, $R_5$, $R_6$, X and Y are as defined in claim 1.

4. A method according to claim 3, wherein, in the specific formula (I-a), $R_1$, $R_2$, $R_4$ and $R_5$ represent a methoxy group, $R_3$ and $R_6$ both represent a hydrogen atom or a methoxy group, X represents:
  either an O(C=O) or NH(C=O) group, in which case y represents a group $NR_9R_{10}$ or $CR_9R_{10}R_{11}$ in which $R_9$, $R_{10}$ and $R_{11}$ represents, independently of each other, a hydrogen atom, a linear or branched $C_1$ to $C_5$ alkyl, $C_2$ to $C_5$ alkynyl group, or alternatively a nitrogen heterocycle selected from the group consisting of pyrollidino and piperidino;

or an NH(C=)O group, in which case Y represents a group $CR_9R_{10}R_{11}$ in which $R_9$, $R_{10}$ and $R_{11}$ represent, independently of each other, a hydrogen atom, a linear or branched $C_1$ to $C_5$ alkyl $C_2$ to $C_5$ alkenyl or $C_2$ to $C_5$ alkynyl group.

5. A method according to claim 1, wherein the piperazine derivative corresponds to the specific formula (I-b):

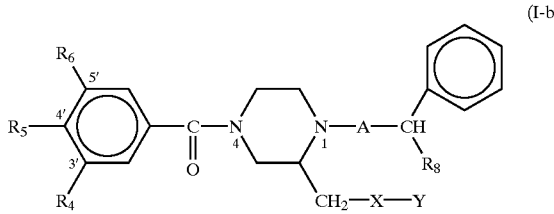

(I-b)

in which $R_8$ represents a hydrogen atom or a phenyl group, while $R_4$, $R_5$, $R_6$, X and Y are as defined in claim 1.

6. A method according to claim 5, wherein, in the specific formula (I-b), $R_4$, $R_5$ and $R_6$ represent a methoxy group, X represents an O(C=O) group, while Y represents a group $NR_9R_{10}$ in which $R_9$ and $R_{10}$ both represent a linear or branched $C_1$ to $C_5$ alkyl, $C_2$ to $C_5$ alkenyl or $C_2$ to $C_5$ alkynyl group, or alternatively a nitrogen heterocycle selected from the group consisting of pyrollidino and piperidino.

7. A method according to claim 1, wherein the piperazine derivative corresponds to the specific formula (I-c):

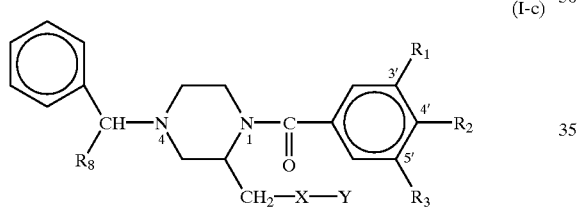

(I-c)

in which $R_8$ represents a hydrogen atom or a phenyl group, while $R_1$, $R_2$, $R_3$, X and Y are as defined in claim 1.

8. A method according to claim 7, wherein, in the specific formula (I-c), $R_1$, $R_2$ and $R_3$ represent a methoxy group, X represents an O(C=O) group, while Y represents a group $NR_9R_{10}$ in which $R_9$ and $R_{10}$ both represent a linear or branched $C_1$ to $C_5$ alkyl, $C_2$ to $C_5$ alkenyl or $C_2$ to $C_5$ alkynyl group, or a nitrogen heterocycle selected from the group consisting of pyrollidino and piperidino.

9. A method according to claim 1, wherein the piperazine derivative is chosen from the group consisting of the following derivatives:

1,4-bis(3',4',5'-trimethoxybenzoyl)-2-(N,N-diethylaminocarbonyloxymethyl)piperazine,
1,4-bis(3',4',5'-trimethoxybenzoyl)-2-(N,N-dipropylaminocarbonyloxymethyl)piperazine,
1,4-bis(3',4',5'-trimethoxybenzoyl)-2-(1'-piperidinocarbonyloxymethyl)piperazine,
1,4-bis(3',4',5'-trimethoxybenzoyl)-2-(1'-pyrrolidinocarbonyloxymethyl)piperazine,
1,4-bis(3',4'-dimethoxybenzoyl)-2-(N,N-diethylaminocarbonyloxymethyl)piperazine,
1,4-bis(3',4',5'-trimethoxybenzoyl)-2-(isopropyloxycarbonylaminomethyl)piperazine,
1,4-bis(3',4',5'-trimethoxybenzoyl)-2-(tert-butylcarbonylaminomethyl)piperazine,
1-benzyl-4-(3',4',5'-trimethoxybenzoyl)-2-(N,N-diethylaminocarbonyloxymethyl)-piperazine,
1-diphenylmethyl-4-(3',4',5'-trimethoxybenzoyl)-2-(N,N-diethylamino-carbonyloxymethyl)piperazine,
1-(3',4',5'-trimethoxybenzoyl)-4-benzyl-2-(N,N-diethylaminocarbonyloxymethyl)piperazine,
1-(3',4',5'-trimethoxybenzoyl)-4-(3',4',5'-trimethoxythiobenzoyl)-2-(N,N-diethylaminocarbonyloxymethyl)piperazine,
1,4-bis(3',4',5'-trimethoxythiobenzoyl)-2-(N,N-diethylaminocarbonyloxymethyl)piperazine and
1-(3',4',5'-trimethoxythiobenzoyl)-4-(3',4',5'-trimethoxybenzoyl)-2-(N,N-diethylaminocarbonyloxymethyl)piperazine.

10. A method according to claim 1, wherein the piperazine derivative is 1,4-bis(3',4',5'-trimethoxybenzoyl)-2-(N,N-diethylaminocarbonyloxymethyl)piperazine.

11. A piperazine derivative corresponding to the general formula (I-a):

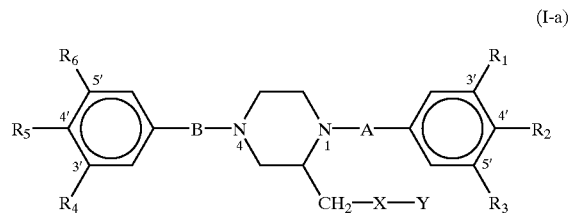

(I-a)

in which A and B represent, independently of each other, a C=O group or a C=S group, while $R_1$, $R_2$, $R_4$ and $R_5$ represent a methoxy group, $R_3$ and $R_6$ both represent a hydrogen atom or a methoxy group, and X represents:

either an O(C=O) group, in which case Y represents a nitrogen heterocycle selected from the group consisting of pyrollidino and piperidino, or alternatively, when $R_3$ and $R_6$ represent a hydrogen atom, a group $NR_9R_{10}$ in which $R_9$ and $R_{10}$ both represent a linear or branched $C_1$ to $C_5$ alkenyl, $C_2$ to $C_5$ alkenyl or $C_2$ to $C_5$ alkynyl group;

or an NH(C=O) group, in which case Y represents either a group $NR_9R_{10}$ or $CR_9R_{10}R_{11}$ in which $R_9$, $R_{10}$ and $R_{11}$ represent, independently of each other a hydrogen atom or a linear or branched $C_1$ to $C_5$ alkyl, $C_2$ to $C_5$ alkenyl or $C_2$ to $C_5$ alkynyl group, or a nitrogen heterocycle selected from the group consisting of pyrollidino and piperidino;

or an NH(C=O)O group, in which case Y represents a group $CR_9R_{10}R_{11}$ in which $R_9$, $R_{10}$ and $R_{11}$ represent independently of each other, a hydrogen atom, a linear or branched $C_1$ to $C_5$ alkyl, $C_2$ to $C_5$ alkenyl or $C_2$ to $C_5$ alkynyl group.

12. A piperazine derivative selected from one of the following compounds:

1,4-bis(3',4',5'-trimethoxybenzoyl)-2-(1'-piperidinocarbonyloxymethyl)piperazine,
1,4-bis(3',4',5'-trimethoxybenzoyl)-2-(1'-pyrrolidinocarbonyloxymethyl)piperazine,
1,4-bis(3',4'-dimethoxybenzoyl)-2-(N,N-diethylaminocarbonyloxymethyl)piperazine,
1,4-bis(3',4',5'-trimethoxybenzoyl)-2-(isopropyloxycarbonylaminomethyl)piperazine, 1-(3',4',5'-trimethoxybenzoyl)-4-benzyl2-(N,N-diethylaminocarbonyloxymethyl)piperazine,
1-(3',4',5'-trimethoxybenzoyl)4(3',4',5'trimethoxythiobenzoyl)2-(N,N-diethylaminocarbonyloxymethyl)piperazine, and
1,4-bis(3',4',5'-trimethoxythiobenzoyl)-2-(N,N-diethylaminocarbonyloxymethyl)piperazine.

13. A piperazine derivative, wherein it is 1-(3',4',5'-trimethoxythiobenzoyl)-4-(3',4',5'-trimethoxybenzoyl)-2-(N,N-diethylaminocarbonyloxymethyl)piperazine, or the pharmaceutically acceptable salts thereof.

14. A piperazine derivative corresponding to the specific formula a (I-b):

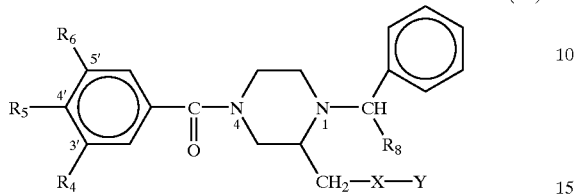

(I-b)

in which:

$R_4$, $R_5$ and $R_6$ represent, independently of each other, a hydrogen atom, a hydroxyl group or a linear or branched $C_1$-$C_5$ alkoxy group;

$R_8$ represents a hydrogen atom or a phenyl group; and

X represents:
either a group chosen from C=O, O(C=O), O(C=S), O(SO$_2$), NH(C=O), NH(C=S), NH(SO$_2$), S(C=O) and S(C=S) groups, in which case Y represents either a group $NR_9R_{10}$ or $CR_9R_{10}R_{11}$ in which $R_9$, $R_{10}$ and $R_{11}$ represent, independently of each other, a hydrogen atom, a linear or branched $C_1$ to $C_5$ alkyl, $C_2$ to $C_5$ alkenyl or $C_2$ to $C_5$ alkynyl group, or Y represents a nitrogen heterocycle selected from the group consisting of pyrollidino and piperidino;

or an oxygen or sulfur atom or a group chosen from O(C=O)O, NH(C=O)O and S(C=O)O groups in which case Y represents a group $CR_9R_{10}R_{11}$ in which $R_9$, $R_{10}$ and $R_{11}$ have the same meaning as above;

or a pharmaceutically acceptable salt thereof.

15. A piperazine derivative according to claim 14, wherein, in the specific formula (I-b), $R_4$, $R_5$ and $R_6$ represent a methoxy group, X represents an O(C=O) group, while Y represents a group $NR_9R_{10}$ in which $R_9$ and $R_{10}$ both represent a linear or branched $C_1$ to $C_5$ alkyl, $C_2$ to $C_5$ alkenyl or $C_2$ to $C_5$ alkynyl group, or alternatively a nitrogen heterocycle selected from the group consisting of pyrollidino and piperidino.

16. A piperazine derivative corresponding to the specific formula (I-c):

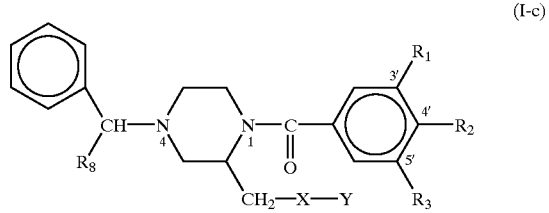

(I-c)

in which:

$R_1$, $R_2$, $R_3$ represent, independently of each other, a hydrogen atom, a hydroxyl group or a linear or branched $C_1$-$C_5$ alkoxy group;

$R_8$ represents a hydrogen atom or a phenyl group;

X represents:
either a group chosen from C=O, O(C=O), O(C=S), O(SO$_2$), NH(C=O), NH(C=S), NH(SO$_2$), S(C=O) and S(C=S) groups, in which case Y represents either a group $NR_9R_{10}$ or $CR_9R_{10}R_{11}$ in which $R_9$, $R_{10}$ and $R_{11}$ represent, independently of each other, a hydrogen atom, a linear or branched $C_1$ to $C_5$ alkyl, $C_2$ to $C_5$ alkenyl or $C_2$ to $C_5$ alkynyl group, or Y represents a nitrogen heterocycle selected from the group consisting of pyrollidino and piperidino;

or an oxygen or sulfur atom or a group chosen from O(C=O)O, NH(C=O)O and S(C=O)O groups in which case Y represents a group $CR_9R_{10}R_{11}$ in which $R_9$, $R_{10}$ and $R_{11}$ have the same meaning as above;

or a pharmaceutically acceptable salt thereof.

17. A piperazine derivative according to claim 16, wherein, in the specific formula (I-c), $R_1$, $R_2$ and $R_3$ represent a methoxy group, X represents an O(C=O) group, while Y represents a group $NR_9R_{10}$ in which $R_9$ and $R_{10}$ each represent a linear or branched $C_1$ to $C_5$ alkyl, $C_2$ to $C_5$ alkenyl or $C_2$ to $C_5$ alkynyl group, or alternatively Y represents a nitrogen heterocycle selected from the group consisting of pyrollidino and piperidino.

* * * * *

UNITED STATES PATENT AND TRADEMARK OFFICE
CERTIFICATE OF CORRECTION

PATENT NO.   : 6,531,476 B1
DATED        : March 11, 2003
INVENTOR(S)  : Heymans et al.

It is certified that error appears in the above-identified patent and that said Letters Patent is hereby corrected as shown below:

Column 5,
Lines 5 to 13, the formula should appear as follows:

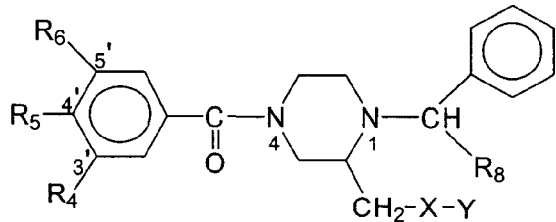

(I-b)

Column 6,
Lines 59 to 67, the formula should appear as:

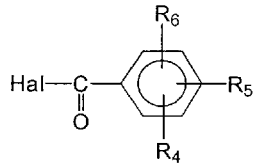

(III-a)

Column 8,
Lines 50 to 65, the formula should appear as:

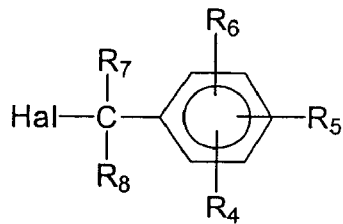

(IV-a)

UNITED STATES PATENT AND TRADEMARK OFFICE
CERTIFICATE OF CORRECTION

PATENT NO. : 6,531,476 B1
DATED : March 11, 2003
INVENTOR(S) : Heymans et al.

It is certified that error appears in the above-identified patent and that said Letters Patent is hereby corrected as shown below:

Column 12,
Lines 42 to 52, the formula should appear as:

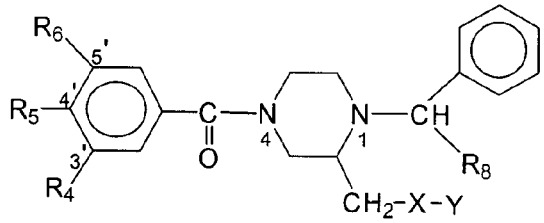

(I-b)

Column 30,
Line 61, "case y" should read -- case Y --;
Line 64, after "alkyl," insert -- $C_2$ to $C_5$ alkenyl or --.

Column 31,
Line 1, "NH(C=)O" should read -- (NH(C=O)O --;
Line 4, after "alkyl", insert -- , --;
Lines 8 to 17, the formula should appear as:

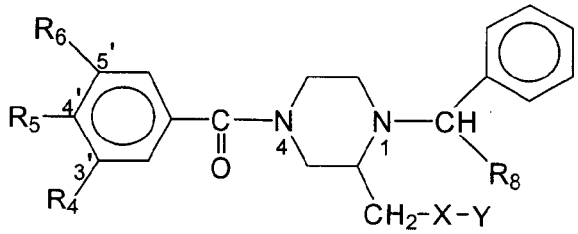

(I-b)

Column 32,
Line 2, after "diethylamino" cancel the hyphen (-);
Line 37, "alkenyl", first occurrence, should read -- alkyl --;
Line 41, after "other" insert a comma (,).

Column 33,
Line 6, after "formula" cancel "a";
Line 34, "(O(C=O)O" should read -- O(C=O) --.

UNITED STATES PATENT AND TRADEMARK OFFICE
CERTIFICATE OF CORRECTION

PATENT NO. : 6,531,476 B1
DATED : March 11, 2003
INVENTOR(S) : Heymans et al.

It is certified that error appears in the above-identified patent and that said Letters Patent is hereby corrected as shown below:

<u>Column 34,</u>
Line 31, "O(C=O)O" should read -- O(C=O) --.

Signed and Sealed this

Twenty-ninth Day of July, 2003

JAMES E. ROGAN
*Director of the United States Patent and Trademark Office*